(12) United States Patent
Wong et al.

(10) Patent No.: US 9,566,186 B2
(45) Date of Patent: *Feb. 14, 2017

(54) PORTABLE MOIST HEAT SYSTEM

(71) Applicants: Vincent York-Leung Wong, Liberty Township, OH (US); Marina Belkin, West Chester, OH (US); Chad Kamil Hickson, Cincinnati, OH (US); Leroy Glenn Owens, Jr., Cincinnati, OH (US)

(72) Inventors: Vincent York-Leung Wong, Liberty Township, OH (US); Marina Belkin, West Chester, OH (US); Chad Kamil Hickson, Cincinnati, OH (US); Leroy Glenn Owens, Jr., Cincinnati, OH (US)

(73) Assignee: Wyeth LLC, New York, NY (US)

(*) Notice: Subject to any disclaimer, the term of this patent is extended or adjusted under 35 U.S.C. 154(b) by 763 days.

This patent is subject to a terminal disclaimer.

(21) Appl. No.: 13/791,324

(22) Filed: Mar. 8, 2013

(65) Prior Publication Data
US 2013/0190553 A1  Jul. 25, 2013

Related U.S. Application Data

(62) Division of application No. 12/454,129, filed on May 13, 2009, now Pat. No. 8,430,921.
(Continued)

(51) Int. Cl.
*A61F 7/08* (2006.01)
*A61F 7/00* (2006.01)
(Continued)

(52) U.S. Cl.
CPC ............ *A61F 7/0085* (2013.01); *A61F 7/034* (2013.01); *A61M 21/02* (2013.01); *A61F 2007/0062* (2013.01); *A61F 2007/0292* (2013.01)

(58) Field of Classification Search
CPC ........................................................ A61F 7/034
See application file for complete search history.

(56) References Cited

U.S. PATENT DOCUMENTS 2,243,110 A   5/1941  Madaras
2,793,946 A   5/1957  Paschal
(Continued)

FOREIGN PATENT DOCUMENTS

EP   0286421   4/1988
EP   1181911   2/2002
(Continued)

OTHER PUBLICATIONS

Terrance Allen, "Methods of Presenting Size Analysis Data", Particle Size Measurement, pp. 153-156 D (4), (1990).
(Continued)

*Primary Examiner* — Kaitlyn Smith
(74) *Attorney, Agent, or Firm* — Keith D. Hutchinson

(57) ABSTRACT

A portable moist heat delivery system comprising a water vapor generating portion comprising a water vapor source and a heat source; a water vapor-air regulating portion, said water vapor-air regulating portion comprising a water vapor-air mixing layer, and a water vapor-air distribution layer; said water vapor generating portion and said water vapor-air regulating portion being in fluid communication; and said water vapor-air regulating portion having a latent heat delivery surface disposed adjacent said water vapor-air regulating portion which delivers moist heat at a preselected temperature range wherein about 15% to about 95% of the moist heat is latent heat of condensation. Methods include delivering improved pain relief, blood flow, relaxation, and reduced cardiac workload.

8 Claims, 3 Drawing Sheets

Related U.S. Application Data

(60) Provisional application No. 61/053,480, filed on May 15, 2008, provisional application No. 61/093,009, filed on Aug. 29, 2008.

(51) Int. Cl.
*A61F 7/03* (2006.01)
*A61M 21/02* (2006.01)
*A61F 7/02* (2006.01)

(56) References Cited

U.S. PATENT DOCUMENTS

| | | |
|---|---|---|
| 2,807,535 A | 9/1957 | Segre |
| 2,900,247 A | 8/1959 | Celada |
| 2,915,379 A | 12/1959 | Agarwal |
| 3,128,174 A | 4/1964 | Celada |
| 3,136,623 A | 6/1964 | Mader et al. |
| 3,136,624 A | 6/1964 | Mader et al. |
| 3,136,625 A | 6/1964 | Mader et al. |
| 3,301,250 A | 1/1967 | Glasser |
| 3,375,098 A | 3/1968 | Marshall |
| 3,423,201 A | 1/1969 | Celada et al. |
| 3,587,578 A | 6/1971 | Walker |
| 3,643,665 A | 2/1972 | Caillouette |
| 3,684,486 A | 8/1972 | Osman |
| 3,765,872 A | 10/1973 | Celada |
| 3,770,421 A | 11/1973 | Celada et al. |
| 3,779,741 A | 12/1973 | Celada et al. |
| 3,816,102 A | 6/1974 | Celada et al. |
| 3,827,879 A | 8/1974 | Celada et al. |
| 3,865,117 A | 2/1975 | Perry, III |
| 3,874,504 A | 4/1975 | Verakas |
| 3,890,142 A | 6/1975 | Celada et al. |
| 3,904,397 A | 9/1975 | Celada et al. |
| 3,940,905 A | 3/1976 | Perry, III |
| 4,055,188 A | 10/1977 | Pelton |
| 4,095,583 A | 6/1978 | Petersen et al. |
| 4,106,478 A | 8/1978 | Higashijima |
| 4,145,184 A | 3/1979 | Brain et al. |
| 4,152,272 A | 5/1979 | Young |
| 4,205,685 A | 6/1980 | Yoshida et al. |
| 4,209,417 A | 6/1980 | Whyte |
| 4,366,804 A | 1/1983 | Abe |
| 4,515,705 A | 5/1985 | Moeddel |
| 4,649,895 A | 3/1987 | Yasuki et al. |
| 4,856,651 A | 8/1989 | Francis, Jr. |
| 4,953,550 A | 9/1990 | Dunshee |
| 5,046,479 A | 9/1991 | Usui |
| 5,062,414 A | 11/1991 | Grim |
| 5,150,707 A | 9/1992 | Anderson |
| 5,179,942 A | 1/1993 | Drulias et al. |
| 5,233,981 A | 8/1993 | Miyashita |
| 5,342,412 A | 8/1994 | Ueki |
| 5,366,491 A | 11/1994 | Ingram et al. |
| 5,366,492 A | 11/1994 | Ueki |
| 5,456,704 A | 10/1995 | Kilcullen |
| 5,471,767 A | 12/1995 | Walker |
| 5,534,021 A | 7/1996 | Dvoretzky et al. |
| 5,545,197 A | 8/1996 | Bowen |
| 5,658,583 A | 8/1997 | Zhang et al. |
| 5,662,624 A | 9/1997 | Sundstrom et al. |
| 5,674,270 A | 10/1997 | Viltro et al. |
| 5,728,146 A | 3/1998 | Burkett et al. |
| 5,741,318 A | 4/1998 | Ouellette et al. |
| 5,823,984 A * | 10/1998 | Silverberg .............. A61F 5/028 128/876 |
| 5,837,005 A | 11/1998 | Viltro et al. |
| 5,860,945 A | 1/1999 | Cramer et al. |
| 5,879,378 A | 3/1999 | Usui |
| 5,904,710 A | 5/1999 | Davis et al. |
| 5,906,637 A | 5/1999 | Davis et al. |
| 5,913,849 A * | 6/1999 | Sundstrom .............. A61F 7/007 602/2 |
| 5,918,590 A | 7/1999 | Burkett et al. |
| 5,925,072 A | 7/1999 | Cramer et al. |
| 5,980,562 A | 11/1999 | Ouellette et al. |
| 5,984,995 A | 11/1999 | White |
| 6,019,782 A | 2/2000 | Davis et al. |
| 6,020,040 A | 2/2000 | Cramer et al. |
| 6,024,761 A | 2/2000 | Barone et al. |
| 6,048,326 A | 4/2000 | Davis et al. |
| 6,074,413 A | 6/2000 | Davis et al. |
| 6,096,067 A | 8/2000 | Cramer et al. |
| 6,099,556 A | 8/2000 | Usui |
| 6,102,937 A | 8/2000 | Cramer et al. |
| 6,123,717 A | 9/2000 | Davis et al. |
| 6,158,427 A | 12/2000 | McGuire et al. |
| 6,261,313 B1 * | 7/2001 | MacWhinnie ............ A61F 7/02 128/890 |
| 6,336,935 B1 | 1/2002 | Davis et al. |
| 6,409,746 B1 | 6/2002 | Igaki et al. |
| 6,436,126 B1 | 8/2002 | McAfee |
| 6,453,648 B1 | 9/2002 | Zhang et al. |
| 6,484,514 B1 | 11/2002 | Joseph et al. |
| 6,629,964 B1 | 10/2003 | Ono et al. |
| 6,652,771 B2 | 11/2003 | Carn |
| 6,666,836 B1 | 12/2003 | Islava |
| 6,791,004 B2 | 9/2004 | Sprengard-Eichel et al. |
| 6,824,557 B2 | 11/2004 | Tone et al. |
| 6,863,682 B2 | 3/2005 | Usui |
| 6,881,219 B1 | 4/2005 | Agarwal et al. |
| 6,893,453 B2 | 5/2005 | Agarwal et al. |
| 7,041,123 B2 | 5/2006 | Stapf et al. |
| 7,060,086 B2 | 6/2006 | Wilson et al. |
| 7,087,076 B2 | 8/2006 | Purcell |
| 7,652,228 B2 | 1/2010 | Igaki et al. |
| 7,878,187 B2 | 2/2011 | York-Leung Wong |
| 8,002,721 B2 | 8/2011 | Bretl et al. |
| 8,343,203 B2 * | 1/2013 | Ishikawa ................ A61F 7/034 424/443 |
| 8,357,189 B2 * | 1/2013 | Ugajin .................... A61F 7/034 607/108 |
| 8,394,134 B2 * | 3/2013 | Hidaka ................... A61F 7/034 607/108 |
| 8,409,154 B2 * | 4/2013 | Mitra ...................... A61F 7/034 132/200 |
| 8,430,921 B2 * | 4/2013 | Wong ...................... A61F 7/034 607/108 |
| 2001/0042546 A1 | 11/2001 | Umeda et al. |
| 2001/0049546 A1 | 12/2001 | Dvoretzky et al. |
| 2002/0020406 A1 | 2/2002 | Minami |
| 2003/0097164 A1 | 5/2003 | Stapf et al. |
| 2004/0015220 A1 | 1/2004 | Um et al. |
| 2004/0042965 A1 | 3/2004 | Usui et al. |
| 2004/0097855 A1 | 5/2004 | Page et al. |
| 2004/0097864 A1 | 5/2004 | Dvoretzky |
| 2004/0116023 A1 | 6/2004 | Huang et al. |
| 2004/0116990 A1 | 6/2004 | Agarwal et al. |
| 2004/0178384 A1 | 9/2004 | Usui |
| 2004/0217325 A1 | 11/2004 | Usui et al. |
| 2004/0261783 A1 | 12/2004 | Madan et al. |
| 2005/0050611 A1 | 3/2005 | Donovan |
| 2005/0222651 A1 * | 10/2005 | Jung ........................ A61F 7/02 607/104 |
| 2006/0173519 A1 | 8/2006 | Matsuo et al. |
| 2006/0276863 A1 | 12/2006 | Kumamoto et al. |
| 2006/0282138 A1 | 12/2006 | Ota |
| 2007/0021810 A1 | 1/2007 | Paulin |
| 2007/0055329 A1 | 3/2007 | Hicks et al. |
| 2007/0068508 A1 | 3/2007 | York-Leung Wong |
| 2007/0106237 A1 | 5/2007 | Carstens |
| 2007/0106242 A1 | 5/2007 | Carstens |
| 2007/0106350 A1 | 5/2007 | Carstens |
| 2007/0106352 A1 | 5/2007 | Carstens |
| 2007/0106353 A1 | 5/2007 | Carstens |
| 2007/0106354 A1 | 5/2007 | Carstens |
| 2007/0106355 A1 | 5/2007 | Carstens |
| 2007/0106356 A1 | 5/2007 | Carstens |
| 2007/0156213 A1 | 7/2007 | Friedensohn et al. |
| 2008/0064996 A1 | 3/2008 | Bretl et al. |
| 2008/0200971 A1 | 8/2008 | Dodo |
| 2008/0234789 A1 | 9/2008 | Freeland et al. |
| 2008/0283038 A1 | 11/2008 | Dodo |

(56) References Cited

U.S. PATENT DOCUMENTS

| | | |
|---|---|---|
| 2009/0062890 A1 | 3/2009 | Ugajin et al. |
| 2009/0222072 A1 | 9/2009 | Robinson et al. |
| 2009/0283106 A1 | 11/2009 | Torgerson et al. |
| 2009/0287168 A1 | 11/2009 | Mitra et al. |
| 2009/0287280 A1* | 11/2009 | Wong ............ A61F 7/034 607/96 |
| 2009/0326622 A1 | 12/2009 | Johnson et al. |
| 2010/0023099 A1 | 1/2010 | Hidaka et al. |
| 2010/0198325 A1* | 8/2010 | Ishikawa ............ A61F 7/034 607/112 |
| 2011/0178585 A1* | 7/2011 | Biser ............ A61F 7/02 607/109 |
| 2012/0022621 A1 | 1/2012 | Wong et al. |
| 2012/0209362 A1 | 8/2012 | Meneses |

FOREIGN PATENT DOCUMENTS

| | | |
|---|---|---|
| EP | 1332740 | 8/2003 |
| EP | 1577363 | 9/2005 |
| EP | 1632202 | 3/2006 |
| EP | 1655005 | 5/2006 |
| EP | 1854436 | 11/2007 |
| GB | 2205496 | 12/1988 |
| GB | 2393732 | 4/2004 |
| JP | 57207748 | 12/1982 |
| JP | 56165223 | 4/1983 |
| JP | 5989029 | 12/1984 |
| JP | 60106874 | 6/1985 |
| JP | H31856 | 1/1991 |
| JP | 6343658 | 12/1994 |
| JP | 8206147 | 12/1996 |
| WO | WO97/01313 | 1/1997 |
| WO | WO97/33542 | 9/1997 |
| WO | WO97/36968 | 10/1997 |
| WO | WO98/29066 | 7/1998 |
| WO | WO03010344 | 2/2003 |
| WO | WO2004061045 | 7/2004 |
| WO | WO2005118740 | 12/2005 |

OTHER PUBLICATIONS

John E. Riedel, "Nonwoven Bonding Methods and Materials", Nonwoven World (1987).

Marilyn Bakker, "Thermoforming", The Wiley Encyclopedia of Packaging Technology, pp. 668-675 (1986).

A. L. Edwards, "A Compilation of Thermal Property Data for Computer Heat-Conduction Calculations", D UCRL-14754, Rev. 1 (May 1, 1968).

PCT/US2005/018262—International Search Report—Date of mailing Oct. 19, 2005 (AMi 03249).

PCT/IIB2006/053443—International Search Report—Date of mailing Oct. 24, 2008. (AMi 03250).

PCT/IIB2006/053444—International Search Report—Date of mailing Mar. 5, 2007 (AMi 03251).

PCT/US2009/043779—International Search Report—Date of mailing Nov. 13, 2009. (AMi 03254).

* cited by examiner

IR Image of External Surface

IR Image of Latent Heat Transfer Surface

PORTABLE MOIST HEAT SYSTEM

This application is a divisional application of U.S. application Ser. No. 12/454,129, now U.S. Pat. No. 8,430,921, filed May 13, 2009, which claims the benefit of U.S. Provisional Applications 61/053,480, May 15, 2008 and 61/093,009, filed Aug. 29, 2008, each of which is incorporated by reference herein in its entirety.

FIELD

The present invention is directed to a portable heat delivery system. In particular, the present invention is directed a portable heat delivery system that generates water vapor and provides moist heat. The present invention also includes methods of making the portable heat delivery system and methods of providing pain relief, deep muscle heating, increased blood flow, reduced cardiac work, relaxation, wound healing, delivery of moisture, delivery of actives, body warming, respiratory relief, skin hydration, enhanced sleep and physical therapy.

BACKGROUND

Disposable heat wraps have become a popular way of applying heat to relieve discomfort of temporary or chronic body aches and pains. Disposable heat wraps typically comprise an exothermic composition for generating heat, wherein the exothermic composition typically comprises metal powder, salts, and water that allows the exothermic composition to release heat upon oxidation of the metal powder. Other disposable or reusable devices can use energy produced by neutralization of acids and bases; heat of hydration of inorganic salts; re-heatable gels; and electrical energy to produce heat. Such devices have been found generally suitable for treatment of aches and pains associated with stiff muscles and joints, nerve pain, back pain, rheumatism, respiratory symptoms and the like. Such devices usually produce heat but contain little moisture.

Some disposable heating devices can provide sustained heat for periods of from about one hour to about twenty-four hours, and are generally described as being less messy and more convenient to use than other conventional heat sources such as whirlpools, hot towels, hydrocollators, heating pads and elastic compression bands. However, there are advantages to delivery of both heat and moisture, such as by a whirlpool or hot towel. Moist heat is often felt to be more soothing and comforting, and can deliver heat and pain relief more quickly than dry heat. However, conventional methods of delivering moist heat, such as hot towels and whirlpools, can be cumbersome and inconvenient and are generally not portable. In addition, certain methods, such as hot towels and some current products that claim to deliver steam heat, can only deliver heat for a short period of time, sometimes 15 minutes or less.

Various approaches of enhancing exothermic reactions in portable heat wrap devices to provide longer heating duration and/or provide heat and moisture include the incorporation of various and different carbon materials such as activated and non-activated carbon materials into the exothermic compositions. Other approaches include the addition of water-retainers or water-holding materials to the exothermic composition to allow excess water to be present and water vapor to be generated.

Other approaches to produce heating devices that provide heat and moisture include attempting to regulate the rate and extent of the exothermic reaction, producing water vapor, regulating temperature of the water vapor, and insulating the skin of a user against the potentially skin-damaging temperature of the water vapor. For example, see U.S. Pat. No. 6,629,964 to Ono. However, most known heating methods and devices for providing heat and moisture provide an inadequate amount of water vapor as the known devices either do not produce an amount of water vapor effective to provide sufficient heat and moisture, particularly in deep muscle tissue; or do not produce water vapor for a long period of time, generally for less than about 4 to 8 hours, often for less than an hour, and typically for about 15 minutes. Further, such devices of the prior art are designed to deliver steam or hot vapor per se.

Further the devices of the known art typically generate water vapor by vaporizing water in an exothermic composition. However, it is known that the thermal performance of typical exothermic compositions containing activated carbon and iron are highly sensitive to and dependent on the water level in the composition. Specifically, an excess level of water in an exothermic heat cell can cause a slow rate of heat up. This is due to water restricting the availability of air needed for the exothermic reaction to occur. Thus, the restriction of air results in slow heating and very little or no water vapor generation. However, by trying to reduce the water level in such a composition in order to achieve a fast heat up rate, the duration of the exothermic reaction can be significantly reduced; i.e. the reaction will quickly end because the activated carbon loses its ability to adsorb oxygen as it dries.

In addition, for a high water vaporization rate, an exothermic composition must get quite hot (>65° C.). Moreover, in order to provide deep muscle heating and effective, sustained pain relief in deep muscle, the deep muscle temperature should be above 38° C. However, because human skin can be damaged at elevated skin temperatures believed by those skilled in the art to be above about 43° C., a heating device must be able to keep the skin temperature of a human user below about 43° C. while providing a high amount of heat to the skin and deep muscle. Thus, a moist heat device must protect the skin from the high temperature of an exothermic composition while delivering high levels of heat, by keeping the skin temperature below about 43° C.

Therefore, despite advances in technology for providing heat and moisture, there remains a need for a portable heating device that provides rapid water vapor generation and heat up, provides sustained water vapor generation, delivers an effective amount of heat to provide deep muscle heating, and maintains the skin temperature below about 43° C.

SUMMARY OF THE INVENTION

The present invention includes a portable moist heat delivery system comprising:
(a) a water vapor generating portion comprising a water vapor source and a heat source; and
(b) a water vapor-air regulating portion, said water vapor-air regulating portion comprising a water vapor-air mixing layer, and a water vapor-air distribution layer; said water vapor generating portion and said water vapor-air regulating portion being in fluid communication; and
said water vapor-air regulating portion having a latent heat delivery surface disposed adjacent said water vapor-air regulating portion which delivers moist heat at a preselected temperature range wherein about 15% to about 95% of the moist heat is latent heat of condensation.

The moist heat delivery system may provide a water vapor-air mixture to the latent heat delivery surface and, wherein said water vapor-air mixture has a dew point temperature of from about 30° C. to about 50° C.

The present invention also includes providing a therapeutic device comprising: a portable moist heat delivery system, the portable moist heat system comprising a water vapor generating portion comprising a water vapor source and a heat source; and a water vapor-air regulating portion, said water vapor-air regulating portion comprising a water vapor-air mixing layer, and a water vapor-air distribution layer; said water vapor generating portion and said water vapor-air regulating portion being in fluid communication; and said water vapor-air regulating portion having a latent heat delivery surface disposed adjacent said water vapor-air regulating portion which delivers moist heat at a preselected temperature range and about 15% to about 95% of the moist heat is latent heat of condensation. The device may be an article selected from the group consisting of back wraps, knee wraps, neck wraps, menstrual wraps, joint wraps, hand/wrist wraps, neck-to-arm wraps, facial wraps, foot wraps, body wraps, blankets, bandages, multi-purpose wraps, patches, pads and combinations thereof.

The present invention includes providing a therapeutic device in which the water vapor generating portion comprises a plurality of water vapor generating heat cells, the heat cells comprising a particulate exothermic composition.

The present invention also includes providing a therapeutic device wherein the heat source comprises a plurality of heat cells at least a portion of said heat cells aligned in a row; and wherein a strip of a foam material overlays said row of heat cells providing an air space parallel to said row of heat cells.

The present invention also includes providing therapeutic device comprising, (a) a portable moist heat delivery system, said system comprising a water vapor generating portion comprising a water vapor source and a heat source, wherein said water vapor source is water absorbed onto a water manager and said heat source is a particulate exothermic composition comprising iron; (b) a water vapor-air regulating portion, said water vapor-air regulating portion comprising at least one water vapor-air mixing layer, and at least one water vapor-air distribution layer, wherein said water vapor-air mixing layer is an aerated structure comprising at least one layer of a material selected from the group of woven materials, non-woven materials and combinations thereof and said water vapor distribution layer comprises at least one layer of a foam material; said water vapor generating portion and said water vapor-air regulating portion being in fluid communication; and said water vapor-air regulating portion having a latent heat delivery surface disposed adjacent said water vapor-air regulating portion which delivers moist heat at a preselected temperature range. About 15% to about 95% of the moist heat is latent heat of condensation.

The present invention also includes a method of providing a benefit to a user comprising: providing a portable moist heat delivery system comprising a water vapor generating portion comprising a water vapor source and a heat source; and a water vapor-air regulating portion, said water vapor-air regulating portion comprising a water vapor-air mixing layer, and a water vapor-air distribution layer; said water vapor generating portion and said water vapor-air regulating portion being in fluid communication; and said water vapor-air regulating portion having a latent heat delivery surface disposed adjacent said water vapor-air regulating portion which delivers moist heat at a preselected temperature range; applying said system to a surface of a user wherein the latent heat delivery surface is located proximate the surface of the user; initiating heating of said system; and transferring moist heat to the skin of the user at a preselected temperature range, wherein the moist heat is about 15% to about 95% latent heat of condensation.

The devices and methods of the present invention, which provide moist heat, can improve the speed of pain relief, increase deep muscle temperature, increase blood flow, and reduce cardiac work. In addition, the devices and methods of the present invention can aid wound healing, provide body warming, deliver actives, deliver moisture to the skin, provide relaxation, provide respiratory relief, enhance sleep, aid in physical therapy of the heated area, promote or enhance post-operative recovery, promote or enhance injury recovery and combinations thereof. The devices and methods of the present invention can also be used for improved, controllable and uniform application of cosmetic and therapeutic compositions to and through the skin and mucus membranes.

BRIEF DESCRIPTION OF THE DRAWINGS

The application file contains at least one drawing executed in color. Copies of this of this patent with color drawings will be provided by the Patent and Trademark Office upon request and payment of necessary fee.

FIG. 5a is a view of the external surface and FIG. 5b is a view of the latent heat delivery surface.

DETAILED DESCRIPTION OF THE INVENTION

Figure 1:
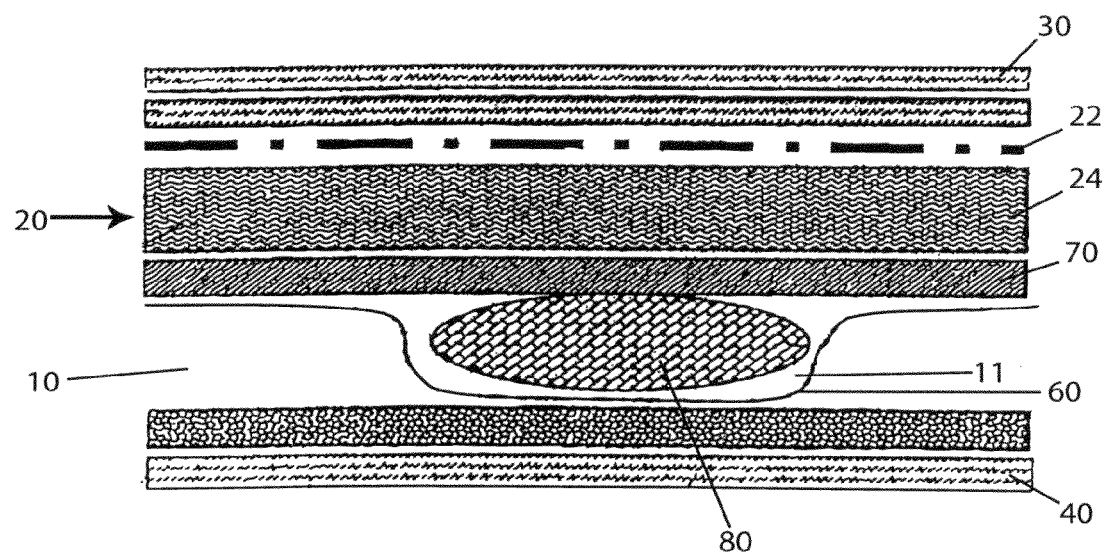
FIG. 1 is a simplified cross sectional schematic diagram of an embodiment of the present invention.

The present invention includes a portable moist heat delivery system comprising: a water vapor generating portion comprising a water vapor source and a heat source; a water vapor-air regulating portion, the water vapor-air regulating portion comprising a water vapor-air mixing layer, and a water vapor-air distribution layer having a latent heat delivery surface disposed adjacent the water vapor regulating portion. The water vapor generating portion and the water vapor-air regulating portion are in fluid communication and air and water vapor can flow within and between the water vapor generating portion and the water vapor-air regulating portion. The latent heat delivery surface is disposed adjacent the water vapor-air regulating portion. The latent heat delivery surface of the moist heat system delivers moist heat at a preselected temperature range and about 15% to about 95% of the moist heat is latent heat of condensation. For a portable moist heat system for use on human skin the preselected temperature should be a temperature that will not damage or burn the skin preferably below about 43° C.

The portable moist heat delivery system of the present invention delivers heat safely and quickly to a human body. The present invention also includes methods for delivering heat safely and quickly to the body, methods for providing deep tissue heating, pain relief, wound healing, reduced cardiac work, relaxation, increased blood flow, delivering moisture, enhanced sleep, physical therapy, and delivering actives. The devices and methods of the present invention can deliver sustained moist heat for up to about 8 hours. The system can be a single-use disposable system or can be incorporated into a reusable or partially reusable system.

The portable moist heat delivery system will be described here in the context of use with a human body. However, as one skilled in the art will appreciate, the portable moist heat system and methods described herein are equally adaptable for use with other animals, plants or inanimate objects recognizing that the maximum temperature of the latent heat delivery surface and the total amount of heat delivered may be adjusted using methods discussed herein to optimize performance for the intended subject. For example, animal body temperatures and sizes may differ substantially from those of a human and thus the selected temperature range and/or amount of moisture to be converted water vapor and/or the number of heat cells used may need to be varied to accommodate the physiology and/or anatomy of the selected species.

The invention can comprise, consist of, or consist essentially of the elements and limitations of the invention described herein, as well as any of the additional or optional ingredients, components, or limitations described herein.

As used herein, "water vapor" refers to water in the gaseous state. "Water vapor-air mixture" and "water vapor-air mixing" refer to adding air to "water vapor" as defined herein. Energy must be added to accomplish the phase change of changing liquid water to water vapor. In the exemplary embodiment discussed herein, heat energy is used. The energy added to accomplish the phase change from liquid water to water vapor is latent heat of evaporation. The latent heat of evaporation energy is released upon on the phase change of condensation of water vapor to liquid water and referred to as latent heat of condensation. The word "steam" as used herein also refers to water in the gaseous state and the terms water vapor and "steam" may be used interchangeably herein with the understanding that "steam" refers only to water vapor not a mixture of water vapor and liquid water droplets.

As used herein "dew point" temperature refers to the temperature to which a water vapor-air mixture must cool before water vapor therein begins to condense.

"Humidity ratio" is the ratio of the weight of water vapor to the weight of dry air.

"Latent heat", as used herein refers to the amount of energy in the form of heat released or absorbed by a substance during a change of phase (i.e. to or from solid, liquid, or gas).

"Moisture", as used herein refers to water.

"Moist heat", as used herein refers to heat wherein about 15% to about 95% of the transferable heat energy is in the form of latent heat of condensation of water vapor. As water vapor and water vapor condensation are associated with moist heat, moist heat includes a moisture component. Moist heat delivery system may also transfer water vapor and, when condensation occurs, and latent heat is released, liquid water. As a moist heat delivery system may in some embodiments operate in conjunction with a another type of heat delivery system, it should be understood that about 15% to 95% of the transferable heat energy in the form of latent heat means for the moist heat delivery system and that this level of production of moist heat should be maintained by the moist heat delivery system for at least about 10 minutes, alternatively, for at least 20 minutes, and alternatively, for at least 30 minutes.

A "pre-selected temperature" as used herein may include the stated temperature plus or minus-1° C. or alternatively plus or minus 2° C., or a maximum temperature (i.e.) a temperature no greater than the stated temperature) or a temperature range with the understanding that the pre-selected temperature means that the temperature behavior is predictable and reproducible under the stated conditions.

The terms "active" or "active agent" and "therapeutic agent" may be use interchangeably herein and include pharmaceutical actives as well as substances that have desired or beneficial effects such as, for example, cosmetic agents or aromatherapy agents.

The term "surface" as used herein may include a surface per se or a layer of layers of a material(s).

The terms "effective amount" or "therapeutically effective amount" of an active agent as provided herein is defined as an amount of the agent at least sufficient to provide the desired therapeutic effect.

The term "median particle size" means that there are as many particles that have a size larger than the designated median size as there are particles that have a size smaller than the designated median size.

Other definitions are provided as necessary as they occur within the description of the invention.

All caliper-measured thicknesses disclosed herein are measured according to ASTM Method No. D5729, unless otherwise specified.

All basis weights disclosed herein are measured according to ASTM Method No. D3776, unless otherwise specified.

All air-permeabilities disclosed herein are measured according to ASTM Method No. D737, unless otherwise specified.

All moisture vapor transmission rates (MVTR) disclosed herein are measured according to ASTM Method No. E96 unless otherwise specified.

All percentages, parts and ratios are by weight, unless otherwise specified. All such weights as they pertain to listed ingredients and components are based on the specific ingredient level and, therefore, do not include carriers or by-products that may be included in commercially available materials, unless otherwise specified.

Moist Heat Delivery System

The physiological benefits of moist heat, such as fast pain relief, deep muscle heating and increased blood flow can only be achieved if a moist heat device delivers a particular, effective amount of moist heat. To facilitate convenient use, it is desirable that a moist heat delivery system be portable. The present invention provides for delivery of an effective amount of moist heat in a portable, convenient, safe moist heat delivery system The portable moist heat delivery system of the present invention includes a water vapor generating portion comprising a water vapor source and a heat source; a water vapor-air regulating portion, the water vapor-air regulating portion comprising a water vapor-air mixing layer and a water vapor-air distribution layer and a latent heat delivery surface. Specifically, the structure is designed to provide water vapor and air mixing and distribution to provide rapid, safe, efficient and sustained moist heat production and transfer.

A cross sectional schematic diagram of an exemplary moist heat system is provided in FIG. 1. Referring to FIG. 1, the system comprises a water vapor generating portion 10, and a water vapor-air regulating portion 20. The water vapor-air regulating portion 20 comprises a water vapor-air mixing layer 24 and a water vapor-air distribution layer 22. As FIG. 1 shows, the water vapor-air regulating portion 20 is interposed between the water vapor generating portion 10 and a latent heat delivery surface 30. The moist heat delivery system shown in FIG. 1 further comprises an external surface layer 40. The external surface 40 is located proximate to the water vapor generating portion 10 and opposite the latent heat delivery surface 30.

In one embodiment the water vapor generating portion generates water vapor which is at a temperature of from about 50° C. to about 70° C. As the water vapor is formed not only is the water vapor warmed but also heat is stored as latent heat of vaporization. In order to generate water vapor, the water vapor source, must heat quickly and deliver a high water vaporization rate for a period of time of at least about 10 minutes preferably about 30 minutes or more. The stored heat of vaporization is released when the water vapor condenses. Water vapor is an ideal candidate to transfer heat because of the magnitude of heat transfer by latent heat when it condenses, and because water vapor is easily generated and available. In exemplary embodiments described herein, heat for generating the water vapor is generated using an exothermic thermal composition such as for example an iron based thermal composition as disclosed in U.S. application Ser. No. 11/233,916. However, as one skilled in the art will appreciate, other thermal materials compositions and/or sources of heat and/or other energy sources may likewise be used to generate heat in the practice of the invention.

In an exemplary embodiment the water vapor generating portion includes thermal composition for generating heat and water available for vaporization. Optionally, these components may be intermixed.

The water vapor-air regulating portion of the moist heat system has multiple purposes and functions. The first function is to allow sufficient air to enter the water vapor generating portion to support the exothermic reaction. Providing sufficient air to support the exothermic reaction is important because the permeable portion of the portable moist heat delivery system is worn against the body. To vaporize the water in the exothermic composition, the temperature of the composition can be as high as about 70° C. However, because human skin can burn at about 43° C., it must be protected from the hot exothermic composition. Thus, in the present moist heat delivery system, as water vapor is generated, it exits the water vapor generating portion through/into the water vapor-air regulating portion. As the water vapor passes through the water vapor-air regulating portion, the water vapor is mixed with air and distributed such that the dew point temperature of the vapor-air mixture is lowered to a preselected temperature range. For general use in humans, this is preferably a temperature that does not harm the skin or other tissue. Conventionally, it is believed that about 43° C. or below is a temperature which will not burn the skin. However, it should be recognized that contact of the skin with a high temperature source will result in a burn only if the skin is unable to dissipate energy it receives. Thus, energy transfer as well as temperature is determinative of the potential for tissue damage. Typically in dry or conductive heat transfer a burn occurs when the skin temperature exceeds about 43° C. However, without wishing to be held to the theory, it is believed that in the case of moist heat much of the energy is transferred via latent heat of condensation. Thus, the temperature of water vapor air mix may be much higher e.g. about 50° C. and the skin will not burn if the amount of energy transferred by the water vapor is insufficient and/or transferred at a rate insufficient to elevate the skin temperature above 43° C. and/or dissipated at a rate sufficient to maintain the skin temperature at about 43° C. or below.

The system of the present invention enables one to use temperatures higher than about 43° C. without harm to human tissue. Previously it was thought that the temperature per se of the water vapor exiting a moist heat device must be lowered to less than about 50° C. as measured by a dry bulb thermometer or thermocouple in order to prevent skin burns. However, the inventors have discovered that potential for tissue damage and/or energy transfer is not reliably reflected in the temperature as measured by conventional dry bulb or thermocouple, but rather is more reliably related to the dew point temperature of the water vapor. Unlike the dry bulb temperature, the dew point temperature is related to the amount of water vapor in the gas mixture. The dew point temperature is determined by the humidity ratio of the water vapor-air mix which is the absolute level of moisture in the air. The relationship of dew point temperature and humidity ratio is that dew point temperature increases as the humidity ratio increases. The energy content of a water vapor-air mixture is more impacted by the amount of water vapor (i.e. stored latent heat) than by its dry bulb temperature (i.e. sensible heat). In regulating the water vapor-air ratio, there may be an incidental decrease in the dry bulb temperature of the water vapor-air mixture. However, regulating the dry bulb temperature of the water vapor-air mixture is not required because the energy gained or lost in a temperature change is significantly less than the energy present as latent heat. Thus, the amount of energy transferred via latent heat can be controlled by regulating the water vapor to dry air ratio. Such a ratio can be expressed as pounds of water vapor/pound of dry air or as kg of water vapor/kg dry air.

As an illustration of the importance of regulating dew point temperature instead of regulating dry bulb temperature points consider exemplary conditions A and B in which conditions A and B have the same enthalpy or energy content but different amounts of water vapor. Condition A is a water vapor-air mixture at its saturation point (maximum water vapor) and has a dry bulb temperature of about 43.3° C. (about 110° F.). Since the mixture is saturated the dry bulb and dew point temperatures are the same. The water vapor-air ratio at condition A is about 0.06 lb water vapor/lb dry air.

Condition B has a lower humidity, or less saturated water vapor-air mix and a water vapor-air ratio of about 0.052 lb water/lb b. In order to have the same energy content as condition A, condition B needs to be at a significantly higher dry bulb temperature (about 60° C.) than condition A. The water vapor-air ratio of about 0.052 lb water/lb dry air of condition B corresponds to a dew point temperature of about 40.6° C. When a water vapor-air mixture such as that of condition B contacts the skin it will not burn the skin at 60° C. since the heat transfer rate is very slow. As it contacts the skin the water vapor-air mix will cool down and condense on the skin at about 40.6° C. (about 105° F.). As it condenses the energy transfer rate will be very high but will not burn the skin since its condensing temperature or dew point temperature is only 40.6° C. In contrast, the water vapor-air mixture of condition A will condense on the skin at about 43.3° C. (about 110° F.) and rapidly transfer its latent heat content. As a result, condition A poses a greater risk of causing skin burn than condition B even though its dry bulb temperature is significantly less that that of the water vapor-air mixture at condition B.

Thus, unlike the prior art, the present invention regulates the water vapor-air mixture ratio as opposed to regulating the dry bulb temperature of a water vapor-air mixture. By regulating the water vapor-air ratio, the condensing temperature or dew point temperature is controlled. When the water vapor-air ratio is regulated to less than about 0.085 lb water vapor/lb dry air the dew point temperature is less than 50° C. Preferably, regulating the water vapor-air ratio to less than about 0.060 lb water vapor/lb dry air will lower the dew point temperature of the water vapor-air mixture to less than 43° C. One of the advantages in controlling the dew point temperature of the moist heat wrap is that the thermodynamics of the system provides a temperature modulation wherein the transfer of latent heat is modulated by the skin temperature (i.e. the latent heat is transferred at the dew point. Thus, transfer will not occur unless the skin temperature is at or below the dew point of the water vapor). This is of particular use for at risk populations whose skin cannot dissipate heat as well as normal population due to low blood flow, high fat content and the like. By controlling the dew point temperature to less than 43° C., skin burns for the at risk population can be prevented since the transfer by latent heat will stop when the skin temperature reaches the dew point temperature.

Thus, in order to avoid skin burn, the amount or ratio of water vapor to dry air must be regulated so that the water vapor condenses at a temperature that does not cause harm to the tissue. For human skin, no harm to tissue will occur if the dew point temperature is less than about 43° C., for example.

For applications in which a higher dew point temperature is desired, such as for some therapeutic applications, the water vapor air ratio may be higher. In these applications the skin temperature may still be below 43° C. since the inventors have surprisingly discovered that there is a significant increase in blood perfusion with the use of the moist heat system of the present invention. Optionally, a high dew point temperature may also be used provided the contact time of the high water vapor-air mix with the skin is short and/or only a portion of the water vapor is allowed to condense at the skin. A short contact time limits the amount of water vapor available to contact the skin. Alternatively, the system may be designed such that a portion of the water vapor is directed to the skin and a portion of the water vapor is allowed to escape the system away form the skin. The contact time and or amount of the water vapor-air mix allowed to contact the skin may be influenced by the wrap design and by the heat cell positions in the wrap.

The portable moist heat delivery system, of the present invention, selectively directs water vapor. In a system intended for human use the water would be direct toward a user's skin. For human use the water vapor reaching the skin would have a dew point at the desired therapeutic dew point temperature of from about 36° C. to about 50° C., alternatively from about 36° C. to about 45° C., alternatively from about 36° C. to about 43° C. alternatively from about 36° C. to about 42° C., alternatively from about 38° C. to about 42° C. and alternatively from about 38° C. to about 40° C. The system can direct water vapor to the selected target for a period of from about twenty seconds to about eight (8) hours, alternatively from about twenty minutes to about five (5) hours, and alternatively from about one half (½) hour to about two (2) hours. For human use, the maximum skin temperature and the length of time of maintaining the skin temperature at the maximum skin temperature may be appropriately selected for a person needing such treatment such that the desired therapeutic benefits are achieved without any adverse events such as skin burns. The water vapor-air regulating portion ensures that a therapeutic amount of moist heat is delivered to a user's skin without adverse effects.

The water vapor-air regulating portion of the moist heat system has a water vapor air mixing layer and a water vapor air distribution layer. Further, as a function of the water vapor-air regulator is to adjust the proportion of water vapor to air, the water vapor-air regulating portion must be in fluid communication with the water vapor generation portion with water vapor passing freely between the water vapor air generation portion and the water vapor-air regulator portion. In an exemplary embodiment, the water vapor-air regulation portion is adjacent the water vapor generation portion. Additionally, the water vapor-air regulating portion needs a supply of air to accomplish the water vapor-air ratio adjustment but as a specific ratio or ratio range is desired regulation of the air supply is desirable. Air supply may be regulated, for example, by control of the density and/or porosity of the materials used to construct the system or, alternatively, by the use of channels and apertures in water and/or air impermeable materials.

The interface between the water vapor-air regulating portion and end user is the latent heat delivery surface. In the case of exemplary human applications, this would be the surface of the moist heat delivery system that is proximate the human skin. In some embodiments that latent heat delivery surface may contact or partially contact the skin surface. In other embodiments, it may be desirable to have a small air gap between the latent heat delivery surface and the skin. In the moist heat delivery system the generated water vapor is preferentially directed toward the latent heat delivery surface. The water-vapor may be passed though the latent heat delivery surface to the user, water-vapor may condense at the latent heat delivery surface transferring the latent heat energy to the user or, alternatively, a combination of water vapor condensation and water-vapor transfer may occur.

The terminology of latent heat delivery "surface" has been selected. However, surface is not intended to be limited to any particular geometric shape, and includes, but is not limited to, planar surfaces, contoured surfaces, and irregular surfaces. The latent heat delivery surface may comprise a layer of material. Optionally, the latent heat delivery surface may be integrally attached to the water vapor-air regulator portion, and/or a surface of a portion of the water vapor-air regulator portion. Alternatively the latent heat delivery surface may be a part of a reusable holder for the system, for example.

Water Vapor Generating Portion

The water vapor generating portion of the present invention contains at least one water vapor source and a heat source. The water vapor source can generate energy and water vapor in any number of ways. Non-limiting examples of heat sources include by chemical energy; energy produced by neutralization of acids and bases; heat of hydration of inorganic salts; repeatable gels; and electrical energy. Water vapor sources can be combined with a heat source. For example an exothermic heat cell can include a mixture of fuel (i.e., heat source) and water and/or water held in a water manager, as the water vapor generating portion of a moist heat delivery system. Alternatively, the water and fuel (i.e., heat source) can be separated with the water being supplied from a reservoir or applied to a surface such as the skin and then contacted with the heat produced by the heat generating source. In water vapor generating portions that comprise energy sources that are not compatible with water, such as, for example, an electrical element, the energy source can be used to heat separate water-containing elements to produce water vapor. A non-limiting example of a water vapor generating portion useful in the present invention uses an exothermic composition including water in a water manager formed in at least one water vapor generating heat cell. A moist heat delivery system may contain a single heat cell or a plurality of heat cells. A plurality of heat cells is particularly useful in the system of the present invention. A plurality of heat cells allows for flexible systems of various size and shape. In addition, the use of a plurality of heat cells allows for an easy control of the water vapor-air mixing ratio for controlling dew point. For example, the dew point temperature for a fixed water-vapor mixing and aeration design can be increased/decreased by increasing/decreasing the number of heat cells. Surprisingly, the inventors also discovered that the duration of heating and total energy delivered can be controlled by varying the number of heat cells used per unit area of water vapor generating portion. The greater the number of heat cells per area, the longer the duration of heating provided. The fewer number of heat cells per area, the shorter the duration of heat provided. In some embodiments it may be desirable to use a combination of moist heat delivery systems and other types of heat cells such as dry heat cells.

Exothermic Composition

In one exemplary embodiment, the thermal energy for generation of water vapor is provided by an exothermic heat cell comprising a particulate exothermic composition. The exothermic composition comprises a flowable particulate pre-mix and a brine solution. The exothermic compositions disclosed in U.S. patent application Ser. No. 11/233,916, are exemplary of suitable exothermic fuel composition.

Particulate exothermic compositions have both desirable features and certain considerations that must be addressed to achieve the desirable features. For example, the performance of an exothermic heat cell can be impacted by the particle size of the particulate components of the exothermic composition in two main ways. First, variation in particle size of the particulate components of an exothermic composition can lead to particle separation or segregation within an exothermic composition. Particle size directly affects particle mobility and particulate components can vary in their mobility, resulting in particle separation or segregation. Changes in the exothermic composition due to particle segregation can lead to less than optimal and/or desired reaction behavior.

The exothermic compositions defined herein comprise particulate components having defined median particle size ranges such that the exothermic compositions resist particle separation or segregation. It is contemplated, however, that particulate components having median particle size ranges above or below the ranges defined herein are suitable for use in the exothermic compositions defined herein.

The second way that performance of exothermic heat cells can be impacted by the particle size of the particulate components of the exothermic composition is that particle size affects accessibility of air through the particulate exothermic composition. In order to support and sustain a vigorous exothermic reaction for releasing water vapor, the particulate exothermic composition should be porous in order to allow free access of air to the reactants of the particulate exothermic composition. The particulate exothermic composition should be porous even with initially high water content (for high water vapor generation) and remain porous throughout the reaction. To be and remain porous, the particulate exothermic composition needs to have an efficient water manager component and the particle sizes of the components of the exothermic composition should exhibit loose particle packing behavior. Without wishing to be bound to the theory, it is believed that proper porosity and maintaining porosity is an important factor in creating heat cells that have long periods of heat production (i.e., heat production for about 8-24 hours) and in creating a composition that has a consistent, reproducible behavior in a plurality of heat cells.

In one embodiment, the heat cells of the present invention comprise a particulate exothermic composition that provides for reliable heating and accordingly reliable and substantial water vapor generation over time frames of a few minutes to hours when the heat cells are incorporated into portable moist heat delivery systems. The exemplary particulate exothermic composition comprises a particulate pre-mix composition and a brine solution.

Components of the particulate pre-mix composition may include iron powder, carbon, absorbent gelling material, and water, which components are described in detail hereinafter. Components of the brine solution may include a metal salt, water, and optionally a hydrogen gas inhibitor such as sodium thiosulfate. The particulate exothermic compositions defined herein are generally prepared by constructing the particulate pre-mix composition and rapidly dosing the pre-mix with the brine solution to result in the formation of the exothermic composition.

For use in a moist heat device a particulate exothermic composition should have the ability to provide fast initial heating and also provide heat for a sustained period of time. Typical exothermic heat devices known in the Art generally can either provide high levels of heat rapidly but last only a few minutes, or they can provide heat for a sustained period of time, but can take up to about 30 minutes to heat. The present invention provides both rapid and sustained heating achieved in part by the choice of components within the particulate exothermic composition. By way of non-limiting example, by modifying component particle size, the speed of heating, duration of heating and temperature of the exothermic reaction can be controlled.

By way of illustration, one particular method of modifying the exothermic reaction involves using iron powder having a median particle size of about 200 μm and an absorbent gelling material having a median particle size of about 300 μm, wherein the median particle size ratio of absorbent gelling material to iron powder is about 1.5:1. This particular ratio of absorbent gelling material to iron powder provides for an exothermic composition that exhibits rapid initial heating and water vapor generation, which has been difficult to achieve with conventional exothermic compositions. Without wishing to be held to the theory, it is believed that attempts to incorporate a high level of moisture in conventional exothermic compositions results in water in the interstitial particle voids which restricts oxygen flow and slows the rate of initial heating. To keep water out of the interstitial particle void volume a water manager is often incorporated into exothermic compositions to absorb excess moisture. However, most water managers such as vermiculite and absorbent gelling material have particle sizes that are significantly larger than the iron particles due to the common practice in the art of using very fine iron particles based on the belief that the iron oxidation reaction is limited by the surface area of the iron particles. Thus, it has been conventionally believed that small iron particles increase the iron surface area.

However, as the inventors discovered and described in U.S. patent application Ser. No. 11/233,916, porosity is an important factor in reaction rate. Thus, the size disparity between the particles of the water manager and iron can promote particle segregation and tight particle packing, inhibiting the reaction. For example, when the particle size ratio of the water manager to iron particles is greater than about 7:1, tight particle packing and inhibition of the reaction can occur.

Thus, with the present invention, exothermic compositions having a particular median particle size ratio of absorbent gelling material to iron powder are used to achieve the desired packing. The selected particle size distribution and ratio facilitates prevention of excess water in the interstitial particle void volume, and prevention of particle segregation and packing with void volumes such that faster rates of initial heating are achieved. The median particle size ratio of absorbent gelling material to iron powder in the present invention is from about 10:1 to about 1:10, alternatively from about 7:1 to about 1:7, alternatively from about 5:1 to about 1:5, and alternatively from about 3:1 to about 1:3.

Iron

It is believed that the exemplary particulate exothermic compositions defined herein release heat upon oxidation of the iron powder. There is no particular limit to the purity, kind, size, etc. of the iron powder as long as it can be used to produce heat generation via an oxidation reaction with water and air.

The particulate exothermic compositions of the present invention comprise one or more iron powder components at concentrations ranging from about 10% to about 90%, alternatively, from about 30% to about 88%, and alternatively, from about 50% to about 87%, by weight of the dry premix composition. Additionally, the system of the present invention can comprise greater than about 0.1 g iron powder/$cm^3$ of a heat cell.

Non-limiting examples of suitable sources for the iron powder include cast iron powder, reduced iron powder, electrolytic iron powder, scrap iron powder, sponge iron, pig iron, wrought iron, various steels, iron alloys, treated varieties of these iron sources, and combinations thereof.

Sponge iron is one source of the iron powder which may be particularly advantageous due to the high internal surface area of sponge iron. As the internal surface area is orders of magnitude greater than the external surface area, reactivity may not be controlled by particle size. Non-limiting examples of commercially available sponge iron include M-100 and F-417, which are available from the Hoeganaes Corporation located in New Jersey, USA.

Iron powder having a median particle size of from about 50 µm to about 400 µm, alternatively, from about 100 µm to about 400 µm, and alternatively from about 150 µm to about 300 µm are exemplary of sizes suitable for use herein. Other sizes may likewise be suitable so long as the ratio of the median particle size of iron to the median size of absorbent gelling material is such that the size and distribution of particles provides for a particle packing with sufficient void volumes to allow substantially free access of air.

The median particle size of the iron powder, and any other particulate component defined herein, can be determined using a sieve method such as the method disclosed in ASTM Method B214. Generally, the particles are screened through a series of sieves consisting of different sizes, and the weight fraction of particles retained on each screen is measured. The weight fraction of the particles in each screen is then used to construct a cumulative weight distribution curve. The cumulative weight distribution curve is constructed by plotting particle size against the cumulatively added weight percent of particles less than the particle size retained on the next largest sieve. A median diameter is determined from the cumulative weight distribution curve, wherein the median diameter is defined as the particle size that corresponds with 50% of the cumulative weight. Details on constructing a cumulative weight distribution curve is described in "Methods of Presenting Size Analysis Data" in Particle Size Measurement, pages 153-156, 4th Edition, Terrence Allen, (1990).

Carbon

In the exemplary particulate exothermic compositions of an embodiment of the present invention comprise one or more carbon components at concentrations ranging from about 1% to about 25%, alternatively, from about 1% to about 15%, and alternatively, from about 1% to about 10%, by weight of the composition.

Non-limiting examples of carbon suitable for use herein include activated carbon, non-activated carbon, and mixtures thereof. The carbon component has a median particle size of from about 25 µm to about 200 µm, and alternatively from about 50 µm to about 100 µm. Activated carbon is particularly useful. In addition, combinations of the various carbons are also useful.

Activated carbon is extremely porous in the inner structure giving it particularly good oxygen adsorption capabilities. In fact, activated carbon has the ability to adsorb oxygen extremely well when the activated carbon is wetted, thus allowing for the activated carbon to function as a catalyst in the oxidation reaction. In the presence of a high water absorbing material such as for example absorbent gelling material or vermiculite the availability of water to the carbon may be restricted. Thus, it is important that activated carbon be pre-wetted prior to the addition of high water absorbing materials. Without being bound by theory, it is believed that activated carbon should be pre-wetted because of its inability to compete effectively against the high water absorbing material when the particulate pre-mix is dosed with brine. When activated carbon is pre-wetted, heat of adsorption is released such that the water adsorbed by the activated carbon is in a thermodynamically low energy state and thus the water does not migrate from the activated carbon to the high water absorbing material. Therefore, the activated carbon remains wet when the high water absorbing material is added, and is able to function as a catalyst for adsorbing oxygen.

In addition to its catalytic behavior, activated carbon may offer the advantage of serving as an auxiliary water manager for the exothermic reaction and/or adsorb odors such as those caused by the oxidation of iron powder.

Non-limiting examples of suitable carbons include activated carbon prepared from coconut shell, wood, charcoal, coal, bone coal, and the like, and combinations thereof are suitable for use herein, but those prepared from other raw materials such as animal products, natural gas, fats, oils, resins, and combinations thereof are also useful. There is no limitation to the kinds of activated carbon used. However, the preferred activated carbon has good oxygen adsorption capabilities. An example of a commercially available activated carbon is activated carbon available from MeadWestvaco located in Covington, Va., USA.

Additionally, the amount of carbon in the particulate exothermic compositions defined herein should be minimal in order to maximize the interstitial particle void volume. Carbon is typically the finest particle component and excess carbon can result in the carbon filling up the interstitial particle void volume between the larger particles of the other materials. Thus, the amount of carbon needed in an exothermic composition for generating moist heat is generally significantly lower than that used in conventional exothermic compositions because of the relatively high level of absorbent gelling material used herein. Therefore, the carbon herein is mainly used for its catalytic activity and minimally for its water retention property.

A low level of pre-wetted carbon is also highly desirable for high speed manufacture of the heat cells of the present invention because a low level of pre-wetted carbon enables the pre-mix to readily absorb the brine solution. With a high level of carbon, the brine absorption rate is slow due to wetting of the carbon. Thus, a low level of pre-wetted carbon significantly increases the rate of manufacture of the heat cells defined herein.

Absorbent Gelling Material

The particulate exothermic compositions of the present invention comprise one or more absorbent gelling materials at concentrations ranging from about 1% to about 25%, alternatively, from about 1% to about 15%, and alternatively, from about 1% to about 10%, by weight of the composition.

The absorbent gelling material ("AGM") suitable for use herein enables the retention of water physically or chemically within the particulate exothermic compositions of the present invention. In particular, the absorbent gelling material serves the function of storing water for release and releasing the water in a controlled manner. Upon heating, stored water is released from the AGM and is converted to water vapor by absorbing heat, thus, storing heat energy as latent heat of vaporization in the water vapor. Additionally, a portion of the stored water may be utilized to maintain the activated carbon moisture level. By storing excess water in the AGM instead of the interstitial particle void volume, the exothermic composition in the heat cell is able to rapidly oxidize the iron and generate an internal temperature high enough to produce water vapor generated from the water stored in the AGM. Because of the AGM's high water holding capacity, the exothermic composition in the heat cells remains highly reactive over a sustained period of time. While not wishing to be bound by theory, it is believed that the AGM can prevent or inhibit liquid water from entering and/or being maintained in the interstitial voids of particulate exothermic compounds, thereby facilitating prevention of "flooding" of the exothermic composition.

Non-limiting examples of suitable absorbent gelling materials include those absorbent gelling materials that have fluid-absorbing properties and can form hydrogels upon contact with water. An example of such an absorbent gelling material is the hydrogel-forming, absorbent gelling material that is based on a polyacid, for example polyacrylic acid. Hydrogel-forming polymeric materials of this type are those which, upon contact with liquids such as water, imbibe such fluids and thereby form the hydrogel. These particularly useful absorbent gelling materials generally comprise substantially water-insoluble, slightly cross-linked, partially neutralized, hydrogel-forming polymer materials prepared from polymerizable, unsaturated, acid-containing monomers. In such materials, the polymeric component formed from unsaturated, acid-containing monomers can comprise the entire gelling agent or can be grafted onto other types of polymer moieties such as starch or cellulose. Acrylic acid grafted starch materials are of this latter type. Thus, specific suitable absorbent gelling materials include hydrolyzed acrylonitrile grafted starch, acrylic acid grafted starch, polyacrylate, maleic anhydride-based copolymer, and combinations thereof. The polyacrylates and acrylic acid grafted starch materials are particularly useful. Non-limiting examples of commercially available polyacrylates include those polyacrylates which are available from Nippon Shokubai located in Chattanooga, Tenn., USA.

The absorbent gelling material has a median particle size of from about 300 μm to about 800 μm, alternatively from about 400 μm to about 800 μm, and alternatively from about 500 μm to about 800 μm. Absorbent gelling materials having a median particle size of 300 μm or greater have been shown to contribute to minimal or no particle segregation effects. Reducing segregation effects provides for improved sustained temperature such that the desired therapeutic heat benefits are achieved without adverse events such as skin burns. Reducing segregation effects also allows for the high-speed production of portable heat delivery devices comprising a plurality of heat cells and that provide for up to five hours of moist therapeutic heat.

As described above, the particulate exothermic compositions defined herein have particular median particle size ratios of absorbent gelling material to iron powder. It has been found that exothermic compositions comprising the defined select median particle size ratios of these components exhibit minimal or no segregation effects which result in exothermic compositions that meet the intended thermal behavior for the desired therapeutic moist heat benefits.

In addition to the absorbent gelling material, the particulate exothermic compositions of the present invention can optionally comprise other water-holding materials that have capillary function and/or hydrophilic properties. These optional water-holding materials can be included in the particulate exothermic compositions at concentrations ranging from about 0.1% to about 25%, alternatively from about 0.5% to about 20%, and alternatively from about 1% to about 15%, by weight of the composition. Non-limiting examples of such optional water-holding materials include vermiculite, porous silicates, wood powder, wood flour, cotton, paper, vegetable matter, carboxymethylcellulose salts, inorganic salts, and combinations thereof. Absorbent gelling material and optional water-holding materials are further described in U.S. Pat. Nos. 5,918,590 and 5,984,995.

Metal Salt

The particulate exothermic composition of the present invention comprises one or more metal salts at concentrations ranging from about 0.5% to about 10%, alternatively, from about 0.5% to about 7%, and alternatively, from about 1% to about 5%, by weight of the composition.

Non-limiting examples of metal salts suitable for use herein include those metal salts that serve as a reaction promoter for activating the surface of the iron powder to facilitate the oxidation reaction with air and provide electrical conduction to the exothermic composition to sustain the corrosive (i.e., oxidative) reaction. In general, several suitable alkali, alkaline earth, and transition metal salts exist which can be used, alone or in combination, to sustain the corrosive reaction of iron.

Non-limiting examples of suitable metal salts include sulfates, chlorides, carbonate salts, acetate salts, nitrates, nitrites, and combinations thereof. Specific non-limiting examples of sulfates include ferric sulfate, potassium sulfate, sodium sulfate, manganese sulfate, magnesium sulfate, and combinations thereof. Specific non-limiting examples of chlorides include cupric chloride, potassium chloride, sodium chloride, calcium chloride, manganese chloride, magnesium chloride, cuprous chloride, and combinations thereof. Cupric chloride, sodium chloride, and mixtures thereof are particularly useful metal salts. An example of a commercially available sodium chloride includes the sodium chloride available from Morton Salt located in Chicago, Ill. (USA).

Water

The particulate exothermic compositions of the present invention comprise water at concentrations ranging from about 1% to about 50%, alternatively, from about 1% to about 35%, and alternatively, from about 5% to about 33%, by weight of the composition. Water suitable for use herein can be from any appropriate source, non-limiting examples of which include tap water, distilled water, deionized water, or any mixture thereof.

It is known that the thermal performance of exothermic heat cells is highly sensitive to moisture level with a small amount of water giving only short time of reaction and too much water slowing the desired heating rate and/or "flooding" the heat cell and terminating the reaction. In a device that generates moist heat, the challenge is even greater as a supply of water is needed to create the water vapor of moist heat. It has been found, however, that the particulate exothermic compositions with interstitial spaces formed by selection of size and distribution of particle sizes of iron and AGM of the present invention not only provide heat cells that are highly effective in generating high amounts of water vapor exceeding 0.25 grams of water vapor per cell over the course of the reaction, but also provide heat cells that have fast initial heating times to achieve desired temperatures quickly. This is achieved by incorporating a sufficient weight ratio of water to absorbent gelling material such that the particulate exothermic compositions have high internal water retention (preferably with the AGM acting as the principal repository) and high interstitial particle void volumes. The particulate exothermic compositions of the present invention comprise a weight ratio of water to absorbent gelling material of from about 3:1 to about 9:1, and alternatively, from about 4:1 to about 7:1, by weight of the exothermic composition.

The particulate exothermic compositions of the present invention can comprise a high level of water and yet be constructed at lower cell weight levels than current heat cells. Therefore, the exothermic compositions of the present invention are utilized more effectively with high water concentration, and less exothermic composition is needed to achieve the desired amount and duration of water vapor generation.

Optional Components

The exothermic compositions of the present invention can further comprise one or more optional components known or otherwise effective for use in exothermic compositions, provided that the optional components are physically and chemically compatible with the compositional components described hereinabove, or do not otherwise unduly impair product stability, aesthetics, or performance.

Optional components suitable for use herein include materials such as agglomeration aids for agglomeration of particles, non-limiting examples of which include corn syrup, maltitol syrup, crystallizing sorbitol syrup, and amorphous sorbitol syrup; dry binders, non-limiting examples of which include microcrystalline cellulose, microfine cellulose, maltodextrin, sprayed lactose, co-crystallized sucrose and dextrin, modified dextrose, mannitol, pre-gelatinized starch, dicalcium phosphate, and calcium carbonate; oxidation reaction enhancers non-limiting examples of which include elemental chromium, manganese, copper, and compounds comprising said elements; hydrogen gas inhibitors, non-limiting examples of which include inorganic and organic alkali compounds, and alkali weak acid salts, specific non-limiting examples of which include sodium thiosulfate, sodium sulfite, sodium hydroxide, potassium hydroxide, sodium hydrogen carbonate, sodium carbonate, calcium hydroxide, calcium carbonate, and sodium propionate; fillers non-limiting examples of which include natural cellulosic fragments including wood dust, cotton linter, and cellulose, synthetic fibers in fragmentary form including polyester fibers, foamed synthetic resins such as foamed polystyrene and polyurethane, inorganic compounds including silica powder, porous silica gel, sodium sulfate, barium sulfate, iron oxides, and alumina; anti-caking agents non-limiting examples of which include tricalcium phosphate and sodium silicoaluminate; and mixtures thereof.

Such components also include thickeners, non-limiting examples of which include cornstarch, potato starch, carboxymethylcellulose, and alpha-starch; and surfactants, non-limiting examples of which include anionic, cationic, nonionic, zwitterionic, and amphoteric surfactants. Still other optional components can be included within the compositions or systems herein, as appropriate, including extending agents, non-limiting examples of which include metasilicates, zirconium, and ceramics, and mixtures thereof. The optional components can be included in the particulate exothermic compositions at concentrations ranging from about 0.01% to about 35%, and alternatively from about 0.1% to about 30%, by weight of the composition.

Oxygen is necessary for the oxidation reaction to occur. However, in the exemplary embodiments presented herein an internal oxygen source is not required. Optionally, in other embodiments within the scope of this invention, oxygen-producing chemical material may be incorporated in the particulate exothermic composition at the time of preparation thereof. Non-limiting examples of oxygen sources suitable for use with the present invention include air and artificially made oxygen of various purity. Air is particularly useful because it is convenient and inexpensive.

Heat Cells

The heat cells of the water vapor generating portion of the present invention can comprise particulate exothermic compositions that utilize an exothermic iron oxidation reaction system to provide a water vapor source. A heat cell comprised of a particulate exothermic composition and used as a water vapor source to deliver moist heat should have a particulate exothermic composition capable of remaining highly reactive even with high water content. High water content provides high rate of water vapor generation for an extended period of time. The particulate exothermic composition provides rapid water vapor generation when incorporated into a water vapor generating portion of portable moist heat delivery systems. The water vapor generation portion is in communication with the water vapor-air regulation portion which adjusts the dew point of the water vapor to a preselected temperature by regulating the proportion of water vapor and air in the water vapor air mixture. For human use the preselected dew point temperature is preferably one that will not harm the human tissue.

The exothermic compositions of the present invention are particulate exothermic compositions. As used herein "particulate" refers to separate particles contained within the compositions. The particulate exothermic compositions defined herein contain separate particles wherein each particle has a median particle size ranging from about 25 μm to about 800 μm. A range of particle sizes is preferred to yield a composition with interstitial pore space.

In an exemplary embodiment, an exothermic composition is prepared by preparing a premix of wetted carbon iron and AGM which is subsequently treated with a brine solution. In one exemplary embodiment the composition comprises from about 10% to about 90% by weight of iron powder; from about 1% to about 25% by weight of a carbon selected from the group consisting of activated carbon, non-activated carbon, and mixtures thereof; from about 1% to about 25% or alternatively about 2% to about 12% by weight of an absorbent gelling material; and from about 1% to about 50%, alternatively from about 1% to about 35% or alternatively from about 15% to about 35% by weight of water. An exemplary single heat cell of the present invention can comprise from about 0.4 g of pre-mix per cell to about 2.5 g of pre-mix per cell, and from about 0.4 g of brine solution per cell to about 1.5 g of brine solution per cell. A heat cell of the present invention can comprise a total cell weight, per cell, of from about 0.8 g to about 10.0 g, alternatively from about 1.5 g to about 3.5 g, and alternatively from about 2.5 g, to about 3.0 g. In an exemplary embodiment, of a moist heat delivery system a plurality of heat cells may be used for constructing a system.

As described above, selection of the particle size of the particulate components particularly the iron and AGM of exothermic compositions is important for minimization of particle separation or segregation within an exothermic composition. Particle size directly effects particle mobility and particulate components can vary in their mobility resulting in particle separation or segregation. The exothermic compositions defined herein preferably comprise particulate components having defined median particle size ranges such that the exothermic compositions resist particle separation or segregation.

It is contemplated, however that particulate components having median particle sizes ranges above or below the ranges defined herein are suitable for use in the exothermic compositions defined herein.

The heat cells of the present invention are small compared to most conventional commercial heat cells, as particle size selection minimizes the need for excess levels of exothermic composition to compensate for particle segregation effects. As described above, particle segregation effects are reduced in the particulate exothermic composition of the present invention by using iron powder in a particular ratio with absorbent gelling material. Further, without being bound by theory, it is believed that the oxidative reaction rate of such exothermic compositions is controlled by the porosity of the exothermic composition. The accessibility of oxygen through the particulate exothermic composition is affected by the packing behavior of the particles, i.e. the interstitial void volume, and by the amount of water present in the exothermic composition. The particle packing behavior is at least in part determined by the relative particle sizes and the distribution of sizes of the particles.

In an exemplary embodiment, the heat cell is formed in a unified structure comprising at least two opposed surfaces, preferably, one substantially non-air-permeable and non-moisture-permeable surface, such as a film layer substrate material and one aerated surface that is highly air-permeable and moisture-permeable, such as a polymer non-woven material. To direct water vapor toward the skin, the air and moisture permeable side of the heat cell is disposed toward the latent heat delivery surface side of the moist heat delivery system. In one embodiment, the air and moisture permeable surface is interposed between the between the heat cell and the water vapor-air regulating portion of the moist heat delivery system and the water vapor-air regulating portion is interposed between the heat cell and the latent heat delivery surface. The substantially non-air-permeable surface may either be the external surface or oriented proximate the external surface.

Uniform heating and water vapor generation may be provided by using a plurality of heat cells. By using a plurality of heat cells, the size of an individual heat cell can be reduced. The relatively small size of the heat cells and their spacing in the system of the present invention enable even air flow to the heat cells. In addition, the water vapor generated can be controlled by the number of heat cells used, and their spacing. By way of non-limiting example, in one exemplary embodiment, two portable heat delivery systems of the same size and composition (e.g. the same in all respects except number of heat cells and the spacing between the heat cells), a system made with 24 heat cells had a water vapor generation rate that was less than two times the water vapor generation rate of a system made with 12 heat cells, yet lasted four times as long. Without being bound by theory, the non-linear water vapor generation and duration relationship is believed to be due to the fixed surface area of the system that is accessible to air. Thus, reaction rate, water vapor generation rate and duration of heat generation can be controlled by the number of heat cells used and their spacing within a given area.

The Aerated Surface

The aerated surface of the heat cells (e.g. "aerated heat cell surface") can serve a dual function of providing air to the particulate exothermic composition in the water vapor generating portion and preventing the particulate exothermic composition from leaking out of the heat cell, as well as forming a water vapor-air mixing layer as part of the water vapor-air regulating portion. The aerated surface impacts regulation of mixing of water vapor and air, particularly when the system is used in a vertical orientation against the skin as the aerated surface is oriented towards the skin in an exemplary embodiment. Variation of the aerated skin-facing surface can thus be used to regulate the amount of air mixed with the generated water vapor to help lower the dew point temperature of the water vapor-air mixture. However, because of its high air permeability the aerated surface has no limiting effect on the reaction rate, and particularly the water vapor generation rate, of the system.

The aerated heat cell surface can be formed of an SMMS (spunbond-meltblown-meltblown-spunbond) material, a SMS (spunbond-meltblown-spunbond) material, a spunbond material, a melt-blown material, mesh, woven fabric and combinations thereof that can vary in basis weight from about 15 gsm (grams per square meter) to about 90 gsm, and alternatively from about 15 gsm to about 76 gsm. In an SMMS material, the "S" layers in the structure provide strength and air entry, while the two "M" layers are made of much finer denier filaments that function to prevent the smaller carbon particles from leaking out of the cells. Non-limiting examples of suitable materials used for an SMMS layer include polypropylene, polyethylene, polyester or other suitable polymer materials known to those skilled in the art.

The aerated heat cell surface can have an air-permeability of greater than about 25 $cm^3/cm^2/sec$ and can have a moisture vapor transmission rate greater than about 5,000 $g/m^2/24H$. The aerated surface can have a thickness of from about 0.05 mm to about 1 mm, alternatively from about 0.1 mm to about 0.8 mm, and alternatively of about 0.4 mm The Opposed Surface of the Heat Cell The opposed, non-air or semi-air permeable/non-moisture or semi-moisture permeable surface of the heat cell can be made of films or films laminated to non-woven fabrics to form a film layer substrate. In general, suitable films are those having heat sealability and are capable of being easily thermally fused. Non-woven materials, if used, provide support and integrity to the film layer substrates. Non-limiting examples of suitable films include polyethylene, polypropylene, nylon, polyester, polyvinyl chloride, vinylidene chloride, polyvinylidene chloride, polyurethane, polystyrene, saponified ethylene-vinyl acetate copolymer, ethylene-vinyl acetate copolymer, natural rubber, reclaimed rubber, and synthetic rubber, and combinations thereof. The film layer substrate has a thickness in the range of about 1 to about 300 μm can be non-air to semi-air permeable and non-moisture to semi-moisture-permeable. For non-woven fabric, if used, those having preferred characteristic properties of light weight and high tensile strength, e.g., nylon, rayon, cellulose ester, polyvinyl derivatives, polyolefins, polyamides, or polyesters, are suitable.

A non-limiting example of a preferred non-woven material is a SMMS laminated structure of from about 15 gsm to about 100 gsm (grams per square meter) basis weight. Such non-woven materials are generally described in Riedel "Nonwoven Bonding Methods and Materials", Nonwoven World, (1987). An example of a commercially available non-woven sheet is material number W502FWH, which is commercially available from FQN (First Quality Nonwoven)) located in Haxie Township, Pa., U.S.A.

Non-limiting examples of useful film layer substrates include polypropylene non-woven sheets laminated to a film of poly(ethylene-vinyl acetate) or low-density polyethylene (LOPE) having a thickness of from about 5 μm to about 100 μm. An example of a commercially available polypropylene/ethylene vinyl acetate (PP/EVA) film is material number DH245, which is commercially available from Clopay Plastics of Cincinnati, Ohio U.S.A.

The heat cell can be formed by bonding opposed surfaces of the aerated surface material and the non/semi-permeable film together around their periphery thereby forming a pouch, envelope, or pocket. Pockets can also be made in the non/semi-air and non/semi-moisture permeable substrate by vacuum, thermoforming, mechanical embossing, vacuum embossing, or other acceptable means. Preferred for use herein is thermoforming which is described in "Thermoforming", The Wiley Encyclopedia of Packaging Technology, pp. 668-675 (1986), Marilyn Bakker, Ed.

When filled with a particulate exothermic composition, each heat cell has a fill volume, void volume, and a cell volume. The fill volume, as used herein, means the volume of the particulate composition in the filled heat cell. The void volume, as used herein, means the volume of the cell left unfilled by the particulate composition in a finished heat cell, measured without differential pressure in the heat cell and without additional stretching or deformation of the substrate materials. The cell volume, as used herein, means the fill volume plus the void volume of the heat cell. The ratio of fill volume to cell volume is from about 0.7 to about 1.0, alternatively from about 0.75 to about 1.0, more alternatively from about 0.8 to about 1.0, alternatively from about 0.85 to about 1.0, and alternatively from about 0.9 to about 1.0.

A heat cell can also be measured in terms of height or thickness of the heat cell at the point of greatest thickness. In an exemplary embodiment the thickness of a heat cells at the point of greatest thickness is from greater than about 0.2 cm (centimeters) to about 1.0 cm, preferably from greater than about 0.3 cm to about 0.9 cm, alternatively from about 0.4 cm to about 0.8 cm, and alternatively from about 0.5 cm to about 0.7 cm.

The resulting heat cell can have any geometric shape, e.g., disk, triangle, pyramid, cone, sphere, square, cube, rectangle, rectangular parallelepiped, cylinder, ellipsoid and the like. The shape of the heat cell can be elongated in its geometry, with the long axis parallel to the substrates, having a height of from about 0.2 cm to about 5 cm, alternatively from greater than about 0.5 cm to about 1 cm, a width of from about 0.2 cm to about 20 cm, alternatively from about 5 cm to about 10 cm, and a length of from about 1 cm to about 20 cm, alternatively from about 5 cm to about 10 cm, resulting in a cell volume of from about 0.04 $cm^3$ to about 30 $cm^3$, and alternatively from about 1.25 $cm^3$ to about 10 $cm^3$.

Alternatively, the shape can be a disk shaped geometry having a cell diameter of from about 0.2 cm to about 5 cm, of from about 1 cm to about 4 cm, alternatively from about 2 cm to about 3 cm, and a height of from about 0.2 cm to about 1 cm, alternatively from about 0.3 cm to about 0.9 cm, alternatively from about 0.4 cm to about 0.8 cm, and alternatively from about 0.5 cm to about 0.7 cm, resulting in a cell volume of from about 0.0045 $cm^3$ to about 20 $cm^3$, alternatively from about 0.2 $cm^3$ to about 1 $cm^3$.

The heat cell can have a planar view surface area, per cell, of from about 0.03 $cm^2$ about 20 $cm^2$, alternatively from about 0.1 $cm^2$ to about 20 $cm^2$, and alternatively from about 1 $cm^2$ to about 20 $cm^2$. Heat cells with this area per cell are easily incorporated into flexible devices which provide improved conformity with body forms; provide even, uniform heat to a target area; and improve wearer comfort.

The heat cell can have a pre-mix weight of from about 0.4 g of pre-mix per cell to about 2.5 g of pre-mix per cell, alternatively from about 1.0 g of pre-mix per cell to about 2.4 g of pre-mix per cell, and alternatively from about 1.5 g of pre-mix per cell to about 2.3 g of pre-mix per cell. Heat cells with this weight of pre-mix per cell are also easily incorporated into flexible devices and systems which provide improved conformity with body forms; provide even, uniform heat to a target area; and improve wearer comfort.

In one exemplary embodiment of the moist heat system, a plurality of heat cells are used. All of the heat cells may be moist heat generators or a component of a moist heat generator, or alternatively a portion of the heat cells may be moist heat generators or component of moist heat generators used in combination with dry heat cells.

In an exemplary moist heat wrap comprising one or more moist heat delivery systems in which the water vapor source is incorporated into heat cells, the water vapor source may comprise a planar area from about 25% to about 90%, alternatively from about 25% to about 75%, and alternatively from about 25% to about 60% of the total planar area of the wrap.

Water Vapor-Air Regulating Portion

The moist heat delivery system of the present invention contains a water vapor generating portion as described above. The water vapor generating portion preferably selectively directs water vapor toward the water vapor-air-regulating portion. As described above in an exemplary embodiment this may be accomplished using a permeable film on one side of the water vapor generating device and an impermeable film on the other side of the water vapor generating device. The water vapor-air regulator portion provides for adjustment of dew point temperature. The water vapor generating portion is in fluid communication with the water vapor-air regulating portion and reduces the dew point temperature of the water vapor-air mixture exiting the system to a safe temperature for delivery of latent heat to the target user. In the embodiments described herein fluid communication is achieved via a permeable material such as a film or other permeable material. However, as one skilled in the art will appreciate other arrangements which afford fluid communication such as, for example, channels or apertures may be likewise suitable to facilitate fluid communication.

Optionally, the water vapor-air regulating portion may orient water vapor generated by the water vapor generation portion towards the latent heat delivery surface and ultimately the user target. In the case of human therapeutic and beauty applications this means toward a body surface of the user. It is preferable that the latent heat delivery surface either be comfortably held against skin or alternatively held very near the skin with a controlled and preselected amount of gap between the surface and the skin. Accordingly the moist heat delivery system may be held in place by being adhesively adhered to the skin, or alternatively placed in a holder such as, for example, a pocket, a wrap, or a contoured device that is held in place at least partially by conforming to a body surface contour. The holder may hold the water vapor generation portion and/or water vapor-air regulating portion in place against the desired body part. In one exemplary embodiment the water vapor-air regulating portion or alternatively a portion of the water vapor-air regulating portion is included in the structure of the holder. The holder may be a single use disposable holder or a reusable holder. The holder may be held in place by any of a variety of means known in the art including, but not limited to, adhesives, fasteners, ties, interlocking parts, buttons, snaps or combinations thereof.

In an exemplary embodiment, the water vapor-air regulating portion can comprise at least one water vapor-air mixing layer and at least one water vapor-air distribution layer. The layers are arranged such that water vapor and air can pass among and between the layers and the water vapor generating portion. The water vapor-air regulating portion also can facilitate an even flow of air into, and water vapor out of, the water vapor generating portion, particularly when the system is used in a manner that compresses the system. To minimize the effect of compression it is desirable to use a water vapor mixing layer that is resistant to compression. An example of such a material is a needle punched non woven material. The water vapor-air regulating portion can also comprise one or more latent heat delivery surfaces. The latent heat delivery surface may be a surface per se of a portion of the water vapor-air regulating portion or alternatively comprise a layer or layers of material.

The air permeability of the water vapor-air regulating portion comprising the water vapor-air mixing layer, the water vapor-air distribution layer and latent heat delivery surface is from about 25 cm$^3$/cm$^2$/sec to about 8000 cm$^3$/cm$^2$/sec, alternatively from about 300 cm$^3$/cm$^2$/sec to about 8000 cm$^3$/cm$^2$/sec, and alternatively from about 500 cm$^3$/cm$^2$/sec to about 7000 cm$^3$/cm$^2$/sec, measured using ASTM Method No. D737. The moisture vapor transmission rate of the water vapor-air regulating portion is from about 500 g/m$^2$/24 H to about 2,500 g/m$^2$/24 H, alternatively from about 1,000 g/m$^2$/24 H to about 2,000 g/m$^2$/24 H, and particularly greater than about 1400 g/m$^2$/24 H, as measured using ASTM Method No. E96. In an exemplary embodiment the water vapor-air regulating portion may comprise one or more water vapor-air mixing layers and one or more water vapor-air distribution layers.

In one exemplary embodiment, a particularly useful arrangement is to use a single water vapor air distribution layer and a single water vapor-air mixing layer. In this embodiment the moist heat system is incorporated into a moist heat wrap and/or pack. It is critical that the perimeter of the moist heat wrap or pack is heat sealed so that the perimeter of the single water vapor air distribution layer and the single water vapor-air mixing layer of the moist heat system are sealed within the perimeter of the moist heat wrap pack. In a preferred embodiment the water-vapor air distribution layer may be constructed of a foam material in which the base material of the foam is substantially impermeable to air and water vapor but which has channels and/or apertures which allow passage of air and for water vapor. The water vapor air distribution layer comprising a perforated foam layer heat sealed around the perimeter restricts air from coming into the perimeter of the moist heat wrap. As a result, the size and number apertures and/or channels in the water vapor distribution layer acts to regulate the system by allowing sufficient air for generating the water vapor while also allowing the exiting water vapor to easily move out of the wrap toward the skin thus regulating the reaction rate and in turn the amount of water vapor generated. By regulating the amount of water vapor generated, the water vapor regulating portion of the wrap can be simplified. Moreover, for embodiments using thermal cells, regulation of the amount of air for reaction also facilitates the control of the heating of the heat cells so that the cells do not reach an excessively high temperature. In one exemplary embodiment, only a single layer of 1/32 inch foam was needed to allow for both good moist heat production and transfer performance and for safe handling of a replaceable moist heat pack with the hands for removal of the pack from air tight packaging which initiates activation and installation into a reusable heat wrap or holder. A thin moist heat pack that is convenient to handle is desirable for use in a semi-durable moist heat wrap or other semi-durable moist heat device since it allows for safe handling of the disposable moist heat pack and convenient reuse of a portion of the wrap.

In one exemplary embodiment, a particularly useful arrangement is to use two water vapor-air mixing layers and two water vapor-air distribution layers, alternating between the two, with the first water vapor-air mixing layer adjacent the water vapor generating portion. Alternatively a water vapor-air distribution layer can be placed adjacent the water vapor generating portion. Optionally, as described above, a water vapor air mixing layer can also be physically formed in integral association with the water vapor generating portion.

The system of the present invention is designed to allow an exothermic water vapor source to operate at a high temperature, from about 50° C. to about 70° C., to maximize water vapor production while delivering latent heat and moisture to the user at a selected temperature for a human use. For a human user the selected temperature is typically a temperature that does not harm the skin. As water vapor and the condensation of water vapor to release latent heat are important to the energy transfer in a moist heat system, the pre-selected temperature for the moist heat system in a preferred embodiment is the dew point temperature of the water vapor-air mixture proximate the latent heat delivery surface. In exemplary embodiments for human use the dew point temperature may be about 45° C., or alternatively about 43° C., or alternatively about 40° C. wherein about includes temperature varying by +/−1° C. or alternatively by +/−2° C. Thus, the system provides protection from thermal damage to the user and maintains an ideal water vapor generating environment that stores and subsequently releases heat energy.

The inventors have surprisingly discovered that dew point temperatures higher than about 43° C. may be used in some instance without harming the human tissue. It is believed, without wishing to be held to the theory, that this is possible because sufficient latent heat energy delivered to the user's body stimulates circulation and facilitates dissipation of the heat energy to avoid harm. Alternatively, the design of the wrap may modify the contact time of the water-vapor with the skin such that the contact time is insufficient to condense all of the water vapor; hence reducing the energy transfer to the skin.

In an exemplary embodiment the water vapor is made safe for skin contact by regulating the mixture of water vapor and air to a water vapor to dry air ratio of less than about 0.085 lb water vapor/lb dry air. By regulating the ratio of water vapor to air, the water vapor in the water vapor-air mixture will condense at a dew point temperature such that heat can be optimally and safely transferred to a user's skin without the risk of thermal injury. As used herein, "dry air" refers to air with no appreciable water content.

The descriptions herein include an exemplary embodiment using two pairs of water vapor-air mixing layers and two pairs of water vapor-air distribution layers. However as one skilled in the art will appreciate that one or a plurality of two, or more water vapor-air mixing layers and one or a plurality of, two, or more water vapor-air distribution layers or some combination thereof may also be used in the practice of the invention. Adjustment of location, thickness, air permeability, and moisture vapor transmission rate of each layer an/or type of material may be desirable to create a suitable thermal and air mixing environment in embodiments having a plurality of mixing layers and/or distribution layers.

Figure 2:
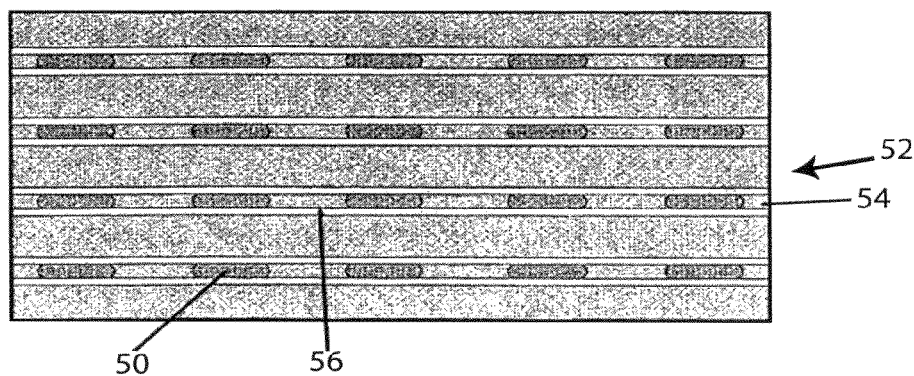
FIG. 2 is a simplified schematic diagram of an embodiment of the present invention.

In one exemplary embodiment, the ratio of water vapor to dry air can be regulated by utilizing one or more longitudinal strips, disposed parallel to a row of multiple heat cells. The strip(s) may function as a portion of the water vapor-air regulating portion. Referring to the simplified schematic drawing in FIG. 2, in an exemplary embodiment, thermal heat cells 50 are aligned in rows on the body of a wrap 52. A foam strip 54 overlays longitudinally each of the row of heat cells 50 forming air channels 56. It is preferable that the strip 54 be positioned in the moist heat system between the heat cells 50 and the latent heat delivery surface in moist heat system. The longitudinal strips can serve to create an air space parallel to a row of multiple heat cells. The air space can aid in providing even flow of air into the water vapor generating portion, and aid in water vapor-air mixing. The height of the longitudinal strips can be adjusted such that the ratio of water vapor to dry air is less than 0.085 lb water/lb of dry air, and alternatively less than about 0.060 lb water/dry air. It is believed without wishing to be held to the theory that a strip over a plurality of heat cells enables the plurality of heat cells covered by the strip to act and/or be impacted cooperatively. In is not necessary that all heat cells be grouped and/or aligned in rows and covered by a strip. In some embodiments only one row or group or a portion of the rows or groupings of heat cells may be covered with a strip.

Water Vapor-Air Mixing Layer

In one exemplary embodiment the at least one water vapor-air mixing layer can comprise an aerated structure of between about 18 gsm and about 430 gsm (grams per square meter), and alternatively about 50 gsm to about 150 gsm. The at least one water vapor-air mixing layer can have a caliper-measured thickness according to ASTM Method No. D5729 of from about 1 mm to about 19 mm, alternatively from about 0.1 mm to about 4 mm, alternatively from about 0.1 mm to about 5 mm and alternatively from about 1 mm to about 4 mm.

Non-limiting examples of materials suitable for the water vapor-air mixing layer include woven materials; non-woven materials including wet-laid, air-laid, point-bonded, needle-punched and thermally bonded non-woven materials; fabrics; polyethylene; polypropylene; polyester; wood pulp; rayon; fibrous plant-based materials including celluloses, wool, silk, jute, hemp, cotton, linen, sisal, ramie; and combinations thereof.

The at least one water vapor-air mixing layer has an air permeability of from about 400 $cm^3/cm^2$/sec to about 17,000 $cm^3/cm^2$/sec, and alternatively from about 1,000 $cm^3/cm^2$/sec to about 1,500 $cm^3/cm^2$/sec, as measured by ASTM Method No. D737, and a moisture vapor transmission rate of from about 5,000 $g/m^2$/24 H to about 7,000 $g/m^2$/24 H, and alternatively from about 5,500 $g/m^2$/24 H to about 6,500 $g/m^2$/24 H, as measured by ASTM Method E96.

Water Vapor-Air Distribution Layer

In one exemplary embodiment, the at least one water vapor-air distribution layer can comprise a layer of insulative material having a caliper-measured thickness, according to ASTM Method No. D5729, of from about 0.1 mm to about 13 mm, alternatively from about 0.5 mm to about 6 mm, and alternatively from about 1 mm to about 2 mm. The at least one water vapor-air distribution layer can have a basis weight of from about 5 gsm to about 430 gsm, alternatively from about 5 gsm to about 50 gsm, and alternatively from about 5 gsm to about 25 gsm, as measured by ASTM Method No. D3776. The material of the water vapor-air distribution layer is substantially air and moisture impermeable, and can be resistant to compression.

Non-limiting examples of materials suitable for the water vapor-air distribution layer include polyethylene-based foam, polypropylene-based foam, polyester-based foam, polystyrene-based foam, polyurethane-based foam, foamed plastic sheet, plastic film, foil, paper-foil laminate, paper, non-woven, sponge, glass wool, fiberglass, and combinations thereof.

The air and moisture impermeable material can have an air permeability of less than about 0.025 $cm^3/cm^2$/sec, measured using ASTM Method No. D737, and a moisture vapor transmission rate of less than about 200 $g/m^2$/24 H as measured using ASTM Method No. E96. The material can also have a thermal conductivity of from about 0.5 W/m*K to about 285 W/m*K (K degrees Kelvin) and a density of from about 5 $kg/m^3$ to about 150 $kg/m^3$. Thermal conductivity of this material can be obtained from the following source: "For Computer Heat-Conduction Properties Data" A. L. Edwards, UCRL-505 Copyright K&K Associates 1997.

In some embodiments, it may be desirable to selectively perforate, the air and moisture impermeable material to form the water vapor-air distribution layer and allow passage of air and water vapor through to the user, and to allow air to enter and to reach the water vapor generating portion, particularly if an exothermic oxidation reaction is used as the mechanism for water vapor generation. Alternatively apertures and/or channels may be employed to allow passage of air and air-water vapor mixtures.

While the materials used for the water vapor-air distribution layer may be substantially impermeable to air and water vapor, they should be assembled, constructed or configured such that the overall air permeability of the vapor-air distribution layer is from about 500 $cm^3/cm^2$/sec to about 2500 $cm^3/cm^2$/sec, alternatively about 1000 $cm^3/cm^2$/sec to about 2500 $cm^3/cm^2$/sec and alternatively about 1500 $cm^3/cm^2$/sec to about 2300 $cm^3/cm^2$/sec as measured by ASTM Method D737. The moisture vapor transmission rate of the vapor-air distribution layer is from about 6,000 $g/m^2$/24 H to about 9,000 $g/m^2$/24 H, alternatively from about 7,000 $g/m^2$/24 H to about 8,500 $g/m^2$/24 H, alternatively from about 7,500 $g/m^2$/24 H to about 8,500 $g/m^2$/24 H, and preferably about 8,100 $g/m^2$/24 H as measured by ASTM Method E96.

Longitudinal Strips

As described above for one embodiment, the water vapor-air regulating portion can also comprise longitudinal strips. Longitudinal strips can be used to provide additional air to the system for reaction and to provide additional water vapor-air mixing. The longitudinal strips can comprise any flexible and non-compressible material. The height of the longitudinal strips can be adjusted to achieve a desired water vapor to air ratio of less than about 0.085 lb water/lb dry air, and alternatively less than about 0.060 lb water vapor/lb dry air. Non-limiting examples of materials suitable for use in the longitudinal strips include polyethylene-based foam, polypropylene-based foam, polystyrene-based foam, polyurethane-based foam, foamed plastic sheet, plastic film, foil, paper-foil laminate, non-wovens, sponge, glass wool, fiberglass, and combinations thereof. The longitudinal strips can be disposed proximate the latent heat delivery surface the system, whether the system is a single-use disposable system, or whether the system is a reusable system. Optionally, for a re-usable system in which a portion of the system is disposable the longitudinal strips can be a portion of either the disposable or reusable portion.

Latent Heat Delivery Surface

The latent heat delivery surface is in communication with the water vapor-air regulating portion and abuts or is adjacent to a target user surface when the system is in use. The latent heat delivery surface may contact the user surface (e.g. the skin in the case of human use) or alternatively be positioned with a predetermined gap between the latent heat delivery surface and the user surface. The latent heat delivery surface may be a surface on a portion of the water vapor-air regulator portion or alternatively a separate layer. In an exemplary embodiment the latent heat delivery surface may be, for example, a layer of material that has a basis weight of from about 20 gsm to about 100 gsm, alternatively from about 40 gsm to about 90 gsm and particularly from about 80 gsm to about 82 gsm. In an exemplary embodiment the latent heat delivery surface may have, for example, a caliper-measured thickness of from about 0.05 mm to about 12 mm, and alternatively from about 0.1 mm to about 5.0 mm, and alternatively from about 0.2 mm to about 2 mm. The latent heat surface can have an air permeability of from about 200 $cm^3/cm^2/sec$ to about 500 $cm^3/cm^2/sec$, alternatively from about 300 $cm^3/cm^2/sec$ to about 400 $cm^3/cm^2/sec$, and particularly about 314 $cm^3/cm^2/sec$ measured using ASTM Method No. D737. The latent heat surface can have a moisture vapor transmission rate of greater than about 5,000 $g/m^2/24$ H measured using ASTM Method No. E96.

Non-limiting examples of suitable materials for the latent heat delivery surface include nylon, rayon, cellulose ester, polyvinyl derivatives, polyolefins, polyamides, polyesters, polypropylenes, celluloses, wool, silk, jute, hemp, cotton, linen, sisal, ramie, and combinations thereof.

Exterior Surface Layer the of System

It is preferable that the exterior surface layer of the system opposing the latent heat delivery surface side (i.e. in a exemplary embodiment for human use the outer side of the water vapor generating portion or surface furtherest from the skin) can comprise an insulative layer that prevents the non-skin facing side of the system from becoming too hot, and that also directs heat downward toward the skin-facing side of the system. The insulative layer can be placed adjacent the opposed side of the heat cells or other water vapor source forming the water vapor generating portion.

Non-limiting examples of materials suitable for an insulative layer include polyethylene-based foam, polypropylene-based foam, polystyrene-based foam, polyester-based foam, polyurethane-based foam, foamed plastic sheet, plastic film, foil, paper-foil laminate, non-wovens, sponge, glass wool, fiberglass, and combinations thereof.

Such an insulative layer can have a caliper-measured thickness, according to ASTM Method No. D5729, of from about 0.1 mm to about 3 mm, alternatively from about 0.5 mm to about 2.5 mm, alternatively from about 1 mm to about 2 mm, and alternatively of about 1 mm.

Such an insulative layer has an air permeability of less than about 0.025 $cm^3/cm^2/sec$ measured using ASTM Method No. D737, and a moisture vapor transmission rate of less than about 250 $g/m^2/24$ H measured using ASTM Method No. E96. The insulative layer also has a thermal conductivity of from about 0.5 W/m*K to about 285 W/m*K (K degrees Kelvin) and a density of from about 5 $kg/m^3$ to about 150 $kg/m^3$. Thermal conductivity of this material can be obtained from the following source: "For Computer Heat-Conduction Properties Data" A. L. Edwards, UCRL-505 Copyright K&K Associates 1997.

An optional one or more outermost layer of material can be added adjacent the insulative layer. Non-limiting examples of such an outermost material include those described above for skin contact layers. The insulative layer and outermost material can also be formed as a pre-combined laminate. Optionally, this outer most layer of material may act as a covering and/or be a part of the structure for holding the device in place in use.

The various layers of the heat generating and/or water vapor-air regulating portion and/or latent heat delivery surface can be bonded together in any number of ways known to those of skill in the art. Non-limiting examples of suitable attachment methods include heat sealing around the periphery of the layers; hot melt glue or adhesive between each layer; spray-on adhesive; ultrasonic bonding/welding; pressure bonding; crimping and combinations thereof. In some embodiments it may be desirable to selectively bond only some of the layers.

Moldable Portion

Optionally, the system of the present invention can also comprise a moldable portion and or be positioned in a molded structure. The moldable portion can provide additional flexibility and stability for use of the system on portions of the body on which it may be difficult to achieve a good fit, such as the face and/or head.

Non-limiting examples of materials from which the moldable portion can be formed include metal foil, metal wire frame structure, flexible plastic structure, flexible laminate structure, and combinations thereof. Such a moldable portion can be incorporated within the structure of the system, or can be an external structure removably or non-removably attachable to an outer surface.

Heat Wraps

The wraps, packs or patches comprising moist heat systems may be self-contained or alternatively placed in a holder. A self contained embodiment may be directly attached to the user such as, for example, by an adhesive or by material extensions that form a wrap that can be secured by lapping, tying or fasteners. It should also be understood that the device may be a single use device or reusable or partially reusable. For reusable devices, replaceable parts such, as for example, the heat source should be conveniently removable, but securable into position for use.

Suitable materials for holders include, but are not limited to, materials listed as suitable for use for the latent heat delivery surface and/or exterior surface layer.

Method of Manufacture
Extothermic Composition Heat Cells

The particulate exothermic compositions of the present invention can be prepared by any known or otherwise effective technique suitable for providing an exothermic composition that provides a moist therapeutic heat benefit. The particulate exothermic compositions of the present invention are preferably prepared using conventional blending techniques such as the blending technique described herein. Other suitable methods of blending the components of the particulate exothermic compositions of the present invention are more fully described in U.S. Pat. No. 4,649,895 to Yasuki et al., issued. Mar. 17, 1987.

In a preferred embodiment, a particular technique of blending the components of the particulate exothermic compositions involves adding carbon to a blender or mixer, followed by adding a small amount of the total water, and then mixing the carbon/water combination. Usually enough water is added to assist in blending while avoiding premature exothermic reaction. Mixing is stopped and an absorbent gelling material is added to the carbon/water combination. Mixing is resumed until all the components are mixed thoroughly, and then iron powder is added and mixed. The composition is then blended until thoroughly mixed to form a particulate pre-mix. Sodium chloride, optionally a hydrogen gas inhibitor such as sodium thiosulfate, and the remaining water are separately mixed to form a brine solution which is then added to the iron powder pre-mix to form a particulate exothermic composition that is useful in the construction of a heat cell of the present invention.

In an exemplary embodiment, heat cells, having two opposed surfaces can be prepared by adding a fixed amount of the particulate pre-mix composition to a pocket in a film layer substrate sheet such as a pocket in a polypropylene/poly(ethylene-vinyl acetate)(EVA) coextruded film layer substrate sheet. In this process, water or brine is rapidly dosed on top of the pre-mix composition, and an aerated structure such as a structure formed of a polypropylene SMMS non-woven substrate is placed over the cell, as a surface opposing and facing the EVA film side of the preformed pocket-containing sheet. The film layer and non-woven layer are bonded together using a low heat, forming a unified structure. The resulting heat cell contains the particulate exothermic composition sealed in the pocket between the film layer and aerated structure.

It has been found that heat cells prepared by the method described herein are especially effective in providing high water vapor generation initially and throughout the desired heat treatment, provided that the heat cells comprise an exothermic composition comprising a select median particle size ratio of absorbent gelling material to iron powder defined herein.

Alternatively, individual heat cells can be prepared by using vacuum to form a pocket. That is, vacuum is used to draw the film layer substrate surface into a mold as the particulate premix composition is placed on top of the film layer substrate surface directly over the mold. The particulate pre-mix composition drops into the vacuum formed pocket which is held in place by the vacuum exerted upon the film in the bottom of the mold. Next, a brine solution is rapidly dosed on top of the pre-mix composition. An aerated structure such as an SMMS polypropylene non-woven substrate surface is then placed over the first film layer substrate surface to form a surface opposing the first film layer substrate surface, such that the particulate exothermic composition is contained between the two opposed surfaces. The particulate exothermic composition is then sealed between the first and second opposed surfaces. Once the heat cells are formed and sealed, the vacuum is released. This particular structure and method of making a plurality of heat cells is particularly advantageous for a moist heat wrap because it eliminates a need to have a separate moisture-impermeable film to keep the generated water vapor directed toward the skin-facing side of the device.

The resultant heat cells can be used individually or as a plurality of heat cells. A plurality of cells is typically desirable for a therapeutic heat treatment. The use of a single heat cell may be useful for a drug delivery application, for example. The heat cells can be incorporated into various portable devices such as disposable and/or reusable body wraps, multi-purpose wraps, bandages, blankets and the like. Some body wraps that can include the moist heat delivery systems such as for example, back wraps, knee wraps, neck wraps, menstrual wraps, joint wraps, hand/wrist wraps, neck-to-arm wraps, facial wraps, foot wraps, body wraps, blankets, bandages, patches, packs, multi-purpose wraps, and combinations thereof can have a means for retaining the wraps in place around/against various parts of the body, The retaining means can include, but are not limited to, adhesives and/or fastening system such as a re-closable two-part hook and loop fastening system, ties, fasteners and the like.

Alternatively, the water vapor generating portion, for example formed of a plurality of heat cells, can be disposable, and fittable into a re-usable device such that a portion of the device is disposable and a portion reusable. By way of non-limiting example, the water vapor generating portion can be disposable and the water vapor-air regulating portion can be reusable.

The resultant heat cells are packaged within 1 to 5 minutes after dosing with the brine solution in a secondary air-impermeable package to prevent the oxidation reaction from occurring until desired, as described in the aforementioned U.S. Pat. No. 4,649,895. Heat cells can also be packaged at a later time provided they are kept in an environment free from oxygen using means known to those skilled in the art such as nitrogen blanketing.

Additional layers can be added or layers can be modified on the skin-facing side of the device, the opposing side, or both as desired for various effects and performance. Examples include but are not limited to, a non woven skin facing layer can be texturized to impart softness or a layer can be impregnated with an aroma or active.

By way of non-limiting example, as described below, one or more insulative layers can be added to either the skin-facing side or the opposing side. Alternatively or in addition, various other layers can be added, as described below, to the skin-facing side of the device. The final structure can be sealed around the perimeter through all of the layers with a perimeter seal, or each layer can be sealed to adjacent layers using sealing systems, non-limiting examples of which include spray-on adhesive, ultrasonic bonding, polymer welding systems, hot melt glue or adhesive between each layer, pressure bonding, crimping, and combinations thereof.

In one exemplary embodiment the heat cells may have different heating output. For example, there can be a combination of high moist heat/short time heat cells with lower moist heat/longer time heat cells. Examples of ways in which the duration of heating of a heat cell may be controlled include, but are not limited to, the amount of exothermic particulate composition material included in the cell and/or the amount of moisture available for forming water vapor. Another exemplary variation is to use one or more moist heat delivery system thermal cells in combination with one or more conventional conduction thermal cells in a single device.

The system of the present invention can optionally incorporate a therapeutic component to be delivered through the skin, wherein the optional therapeutic component includes aromatic compounds, non-active aromatic compounds, cosmetic actives, pharmaceutical actives, moisturization actives, health actives, nutritional supplements, aromatherapy agents, other therapeutic agents, and combinations thereof.

The amounts of such actives can vary, depending on the particular active. The amounts provided by embodiments of the present invention are generally less than those required for dosing through the skin in a dry environment, such as with a dry heat mechanism.

The optional therapeutic component can be incorporated into the water vapor generating portion as a separate substrate layer, incorporated into at least one of the substrate layers forming the heat cells, incorporated into the chemistry contained in the heat cells, incorporated into separate active-containing cells, or incorporated into a separate, discrete device to be used with the water vapor generating portion and water vapor-air regulating portion. The heat cells can also comprise a separate substrate layer, or be incorporated into at least one of the opposing surfaces, a self-adhesive component and/or a sweat-absorbing component.

The invention is amenable to a wide variety of types of active materials including but not limited to, volatile materials, water soluble materials, materials with limited water solubility at ambient temperature and combinations thereof. Further, in some cases water insoluble materials may be utilized in the system such as, for example, when presented to the system in combination with suitable solvents or solubilizers.

Non-limiting examples of active aromatic compounds include aromatherapy agents, menthol, camphor, eucalyptus, and mixtures thereof. Non-limiting examples of non-active aromatic compounds include benzaldehyde, citral, decanal, aldehyde, and combinations thereof. Non-limiting examples of cosmetic actives include moisture-enhancing actives, wrinkle-reducing actives, skin-tone enhancing actives, skin lightening actives, skin darkening actives, and combinations thereof. Non-limiting examples of pharmaceutical actives/therapeutic agents include antibiotics, vitamins, nutritional supplements, herbal agents, antiviral agents, analgesics, anti-inflammatory agents, antipruritics, antipyretics, anesthetic agents, decongestants, mucolytics, antitussives, antihistamines, pain-relieving actives, antifungals, antimicrobials, and combinations thereof. In particular, non-limiting examples of pain-relieving actives include aspirin, salsalate, diflunisal, ibuprofen, ketoprofen, nabumetone, piroxicam, naproxen, dicloenac, indomethacin, sulindac, tolmetin, etodolac, ketorolac, oxaproxin, celecoxib, and combinations thereof.

The present invention has many uses, non-limiting examples of which include delivering consistent, safe, efficient, and sustained moist heat, pain relief, deep muscle heating, increased blood flow, reduced cardiac work, wound healing, body warming, delivery of actives, delivery of moisture, respiratory relief, skin hydration, enhanced sleep, physical therapy, and combinations thereof. The shape, size and form of the system may be varied to facilitate the particular selected use, i.e., body wrap, facial wrap, multi-purpose wrap, bandage, blanket, and the like.

For human use the system safely and efficiently delivers a large amount of latent heat while maintaining a skin surface temperature of from about 36° C. to about 50° C., alternatively about 36° C. to about 45° C., alternatively about 36° C. to about 42° C., alternatively about 36° C. to about 43° C., alternatively from 38° C. to about 42° C., and alternatively from about 38° C. to about 40° C. The system also provides a skin surface temperature of about 36° C. within about 5 minutes of initiation of heating. In addition in one embodiment, the system provides a skin surface temperature of at least 38° C. for at least about 60 minutes as measured by thermocouple.

In one embodiment the system is able to deliver safe heat by adjustment of the dew point temperature of the water vapor-air mixture delivered to the skin surface. The dew point is adjusted by adjusting the proportion of water vapor to air or humidity ratio. In an exemplary embodiment, the water vapor-air mixture has a humidity ratio of water vapor to air that is less than 0.065 lb water vapor/lb dry air, and alternatively, less than about 0.060 lb water vapor/lb dry air, which corresponds to a dew point temperature of from about 40° C. to about 50° C.

Because the temperature of the water vapor-air mixture of the system in use on a body is only a few degrees above normal skin temperature of from about 32° C. to about 35° C., and the dew point temperature of the water vapor-air mixture is approximately that of normal skin temperature when it reaches the skin, heat can be safely transferred to the skin via latent heat of condensation of water from the water vapor-air mixture. Thus, the system is able to safely deliver a large amount of heat to the skin, wherein from about 15% to about 95%, alternatively from about 20% to about 80% and alternatively from about 40% to about 75% of the heat is delivered as latent heat. In a one embodiment, the moist heat system delivers about 15% to about 95% of the heat as latent heat of condensation for at least 10 minutes, alternatively, at least 30 minutes or alternatively, for at least about 1 hour, alternatively, for at least about 3 hours, or alternatively, for at least about 5 hours.

In addition to delivering heat the moist heat system may also provide moisturization to tissues as the water vapor condenses to water and delivers the latent heat of condensation to the tissue.

Skin surface temperature may be measured by the following method. Temperature measurements may be made using a thermocouple. Temperature measurements may be made by positioning a thermocouple between the skin and the latent heat delivery surface. In an exemplary embodiment temperature measurements are made with K-type thermocouples (Omega, part #5SRTC-TT-K-40-72) and recorded by temperature data logger (Omega, HH84). To measure the temperature of the surface of a user's skin, the user sits in a room at about 22° C. for about 20 minutes to normalize the skin to the room temperature and conditions. During that time, a thermocouple is placed and taped on the skin surface, taking care that the tape is not placed over the sensing area of the thermocouple. Upon expiration of the equilibration time, temperature can be measured and recorded for a desired period of time.

To facilitate standardization of the test results in some embodiments is desirable to construct the moist heat system to be measured, seal it in an impermeable container and set it aside for 24 hours to equilibrate before testing. When a system is to be tested, it is removed from the impermeable container/protective packaging to activate the heat cell and placed on a user's body part, typically the forearm or back, with the temperature measurement device, e.g. thermocouple and/or heat flux sensor, touching the body part between the body part and the measurement device. A single measurement may be made or alternatively a series of measurements over time. Typically, skin temperature may be measured before application of the system to be tested and/or after application of the system for reference purposes. This may be accomplished by placing the measurement device on the skin.

All measurements are preferably made at ambient environmental conditions, i.e. a temperature range of about 21° C. to about 23° C. and relative humidity range of about 38% to about 42% in the laboratory or area in which the measurements are made.

The dew point temperature is preferably measured when the moist heat system is activated and in position on a user as the dew point temperature of particular interest is related to the amount of water vapor between the body and the moist heat wrap. The amount of water vapor between the body and the moist heat wrap is dependent on the amount of water vapor generated by the wrap minus the amount of water vapor condensed and the amount of water vapor that flows out of the wrap.

Dew point temperature may be measured with a Vaisala HUMICAP® HMT337 dew point transmitter (Vaisala) with Stainless Steel HM47453SP filter. This unit is manufactured by Vaisala and is obtained from their US office at 10 D Gill St., Woburn, Mass. 01801 Tel 1-888-824-7252. This instrument has a heated humidity probe which prevents condensation on the probe in high humidity environment. To record the dew point temperature the moist heat wrap is activated to begin production of heat and water vapor and placed on the surface of a user. For a human user the skin of the back or forearm is convenient but may be measured at any surface where the device may be used. It is preferable to allow 1-5 minutes for the system to "stabilize" before beginning measurements. To make a measurement the humidity probe is inserted between the moist heat pack and the user surface and allowed to stabilize. The dew point temperature is displayed on the transmitter of the measurement device. The dew point temperature measurement is taken after it has stabilized for about 90 seconds. The probe measures a very localized environment, thus it may be desirable to make multiple measurements at various positions between the wrap and the surface.

The system of the present invention as described herein can generate and deliver from about 75 W/m$^2$ to about 500 W/m$^2$, alternatively from about 100 W/m$^2$ to about 200 W/m$^2$, alternatively from about 200 W/m$^2$ to about 500 W/m$^2$, and alternatively from about 300 W/m$^2$ to about 500 W/m$^2$ of heat flux at a safe skin temperature.

Heat generated and/or transferred may optionally be monitored and/or measured using infrared imaging. An FLIR Systems SC660 Infrared Camera manufactured by FLIR System equipped with FLIR ExaminIR Software for image analysis and a MX 350 24" Tabletop Tripod or similar.

The moist heat system generates and delivers heat to a surface of the skin wherein from about 15% to about 95%, alternatively from about 20% to about 80%, and about 40% to about 75% of the heat delivered to a surface of the skin is delivered as latent heat upon condensation of the water vapor-air mixture. Without wishing to be held to the theory, it is believed that the remainder of the heat transferred to the user is heat transferred by conduction. Because a majority of the heat transfer is through condensation on/in the body through control of the dew point temperature by water vapor-air mixing, the system of the present invention can deliver peak heating levels to the body of up to two to five times that of a conventional dry heating wrap while maintaining constant skin temperature of about 43° C. or less, thereby providing a safe usage experience for the user.

The system produces heat at different rates during the reaction. Initially the system produces water vapor at a very high rate approaching 2.0 mg/min/cm$^2$ of water vapor generation. During this period the rate of heat transfer to the skin is very high as the latent heat of condensation of this amount of water vapor over about the first 30 minutes of system use causes a large increase in heat flux to the skin, thereby increasing deep muscle and skin temperature very rapidly. That the heat is delivered by latent heat of condensation is demonstrated by stable skin temperature that occurs within about 10-60 minutes of applying the system and then stabilizes at an equilibrium dew point temperature between the water vapor and the condensing water vapor at the skin surface. The continued addition of high heat flux to the skin at the constant temperature demonstrates that latent heat is responsible for at least about 15% and up to about 95% of the heat transfer to the deep muscle tissue, while maintaining a constant selected temperature which is less than the temperature that would cause harm or damage to the skin. In an exemplary embodiment for human use a temperature of less than about 43° C., alternatively less than about 41° C., or alternatively less than about 39 C.°.

The increased moisture content of the skin also improves the thermal conductivity of the skin and improves the rate of heat transfer through the skin and deeper into the underlying tissue. Once the initial water vapor generation rate has raised the deep tissue and skin temperature to a therapeutic level the water vapor generating portion is designed such that water vapor generation rates are reduced to a lower level of between about 0.05 mg/min/cm$^2$ and about 1.0 mg/min/cm$^2$. At this lower sustained rate the system continues to produce water vapor that provides enough latent heat to maintain the skin and deep tissue temperature at the desired therapeutic temperature achieved within the first 10-30 minutes of system use for the duration of the system use.

Latent heat can deliver the heat benefit of the system to a user because of the large amount of heat flux, e.g. the ability to supply sufficient heat to raise the temperature of body tissue mass to a therapeutic temperature within 10-30 minutes of initiation of heating of the system without exposing the skin to a damaging temperature; i.e. maintaining a skin temperature of less than about 43° C. This is in contrast to conventional dry heat wraps that rely on conductive heat transfer would require that the skin temperature be raised to above 50° C. to deliver a deep muscle temperature of 38° C. in less than one hour.

In one exemplary embodiment the energy output of a moist heat delivery system of the invention is about 75 W/m$^2$ to about 500 W/m$^2$ heat flux alternatively from about 100 W/m$^2$ to about 300 W/m$^2$ heat flux and alternatively from about 150 W/m$^2$ to about 250 W/m$^2$ as compared to a conventional dry wrap which typically delivers from about 50 W/m$^2$ to about 100 W/m$^2$ of heat flux. This is a difference in heat delivered to the body of about 3 times over the same period of time at a safe application temperature.

Heat flux can be measured by using a PU_22 (Huksaflux, HuksefluxUSA, Inc. P.O. Box 850, Manorville, N.Y. 11949, heat flux sensor. Signals from the heat flux sensor are read with an OM-DAQPRO-5300 logger (Omega Engineering Inc., address: One Omega DR., Box 4047 Stamford, Conn., USA, phone (203)359-1660). The unit is programmed to convert the millivolt signals it receives from the heat flux sensor to W/m$^2$. A USB interface is used to transfer data form the logger to a computer. In an exemplary measurement, the data is recorded for 1 hour at 10 second interval.

In making a measurement, the heat flux sensor(s) is first connected to the logger and data recoding is initiated in the software. The moist heat system to be tested is removed from its sealed storage pouch or container and activated by contact with air. The moist heat system is placed with the side that is releasing water vapor on top of the heat flux sensor. Once the heating device is placed on the heat flux sensor, acquisition of data begins and measurements are then recorded for the desired period of time. The heat flux results are tabulated and can be plotted against time. Such a plot is particularly useful to help define the time intervals representing the maximum heat flux, the steady state heat flux and the interval with decreasing heat flux.

Measurement of Latent Heat

Latent heat released can be determined using the heat flux and water loss/generation rate. For determining the % of total heat of a moist heat system that is latent, the thermal output (e.g. heat flux) of the moist heat wrap is measured when the system is placed with its permeable side facing up. This is done in order to allow the moisture to freely escape from the wrap and not be re-absorbed back to the wrap. To measure the total heat flux the moist heat wrap is placed on top of a heat flux sensor that is attached to the surface of a constant temperature plate maintained at 36° C. in an environment at a temperature of 23° C. and a relative humidity of 40%. The temperature plate is maintained at a constant temperature by circulating water from a temperature controlled circulating water bath available from VWR Scientific, Suwanee, Ga., USA, model 1157, at a rate of 1.3 L/min. A constant temperature plate that can be used is described in JIS S 4100 (Japanese Standards Association).

The water vapor generation rate is determined by measuring the weight change of the moist heat system. The method for determining the water vapor generation rate is described below. To calculate latent heat the water loss rate is multiplied by the latent heat of water which is 2.261 kJ/gm of water.

The heat flux and water loss rate are plotted. Calculation of the % total heat flux that is due to latent heat can be performed by examining graphs of the heat flux and water vaporization rate to determine the time intervals of each that have the maximum heat flux and the longest steady state behavior. Multiple time points may used to calculate a range of heat flux provided because in one embodiment both rapid heating and water vapor generation as well as sustained heating and water vapor generation are provided. Thus, heat flux and water vapor generation can vary over the course of the exothermic reaction.

For one exemplary 24 cell moist heat wrap in which heat was measured at five regularly spaced intervals over a 60 minute time period, the percentage of total heat that was latent heat ranged from about 42% to about 61%. More specifically, the percentage of total heat that was latent heat was 49%, 61%, 61%, 42% and 47% for measurements one to five, respectively. The total amount of heat was about 750 W*min/m², about 2400 W*min/m², about 5000 W*min/m², about 3400 W*min/m², and about 1500 W*min/m² for measurements one to five, respectively. This example is provided solely for the purpose of illustration and should not be construed to be a limitation as many other variations of the present invention are possible.

The heat flux and water vapor loss rate are used to calculate the % heat flux due to latent heat at each time interval. The equation used is shown below:

$$\% \text{ heat from latent heat} = 100 \times \frac{\text{Water vapor loss rate (gm/m}^2\text{min)} \times 2.261 \text{ kJ/gm water}}{\text{Heat flux (kJ/m}^2\text{min)}}$$

$1 \text{ W} = 1 \text{ J/s}.$

The systems and methods of the present invention transfer to the user from about 15% to about 95%, alternatively from about 20% to about 80% and alternatively from about 40% to about 75% of the heat generated as latent heat.

The production and quantity of latent heat transferred by the moist heat system is distinguishable from prior devices marketed as "steam" heat devices which typically when tested by this method show no detectable amounts of latent heat transfer.

The portable moist heat delivery system of the present invention, when applied to the body, also dramatically impacts skin and muscle temperature causing an increase in blood circulation/flow rates in the area where the system is applied. Total cardiovascular work in the body is decreased due to application of the system even though localized blood flow is dramatically increased.

An increase of from about 3 to about 9 times the resting blood flow rate of an area of skin prior to application of the system, during a time period the system is applied to the area of skin of a user, is provided by the system. In an exemplary 24 moist heat cell embodiment, the system increased blood flow about 5 times versus a dry heat wrap, and an exemplary 12 moist heat cell embodiment, the system increased blood flow about 2 times versus a dry heat wrap. Use of an exemplary 24 cell moist heat embodiment of the system for an hour increased the blood flow comparably to a conventional hydrocollator treatment and more than a conventional Whirlpool treatment. This example is provided solely for the purpose of illustration and should not be construed to be a limitation as many other variations of the present invention are possible.

When cardiac workload is measured as a product of mean blood pressure and mean heart rate over a period of time, cardiac workload is decreased by at least about 4% with application of the portable heat delivery system of the present invention to the skin of a human user. Cardiac work is held essentially constant with the application of dry heat wraps or other typical modalities of heating such as hydrocollators. In the case of a whirlpool bath, the cardiac workload increased significantly, by over 20%, during a 15 minute application. The type of cardiac relaxation provided by the present invention was previously unattainable with portable moist heat devices.

Moist heat delivery systems may increase the deep muscle temperature to a temperature well above the typical resting temperature of about 36° C. at 2.5 cm below the skin surface to a temperature of about 38° C. The system also provides a tissue temperature of at least about 38° C. at a depth of at least about 2.5 cm below an outer surface of the skin of a user within about 60 minutes from initiation of heating, while maintaining a temperature of the outer surface of the skin of less than about 43° C.

Furthermore, the system provides an increase in temperature of tissue at least about 2.5 cm below an outer surface of the skin of a user of at least about 1° C. above an initial tissue temperature measurement within about 20 minutes from initiation of heating, while maintaining a temperature of the outer surface of the skin of less than about 43° C.; of at least about 2° C. above an initial tissue temperature measurement within about 40 minutes from initiation of heating, while maintaining a temperature of the outer surface of the skin of less than about 43° C.; and of at least about 3° C. above an initial tissue temperature measurement within about 60 minutes from initiation of heating, while maintaining a temperature of the outer surface of the skin of less than about 43° C.

Deep muscle temperature and skin temperature of a user during use of exemplary 12 heat cell and 24 heat cell embodiments of the moist heating system of the present invention were compared to deep muscle and skin temperatures for a conventional dry thermal heat cell device. The exemplary 24 cell moist heat cell device, heated deep muscle to about 38° C. with a maximum skin temperature of about 40° C. The exemplary 12 cell moist heat cell device heated deep muscle to about 37.5° C. with a maximum skin temperature of about 40° C. The conventional dry heat cell device heated deep muscle to less than about 36.5° C. after 60 minutes of heating with a maximum skin temperature of about 35° C. This example is provided solely for the purpose of illustration and should not be construed to be a limitation as many other variations of the present invention are possible.

Such a deep tissue temperature is typical of the type of thermal heating previously only achievable with the use of whirlpool baths. The type of heating capability provided by the present invention was previously unattainable with portable, moist heat devices.

Skin temperature and deep tissue temperature can be measured by the following methods.

Skin temperature is measured with a thermistor probe, TSD202A produced by BIOPAC, Inc., Goleta, Calif. Such a probe is a "fast response" probe with a response time of 0.6 seconds and is 1.7 mm in diameter. Output of the probe is digitized with an MP100 16 bit ND converter, and stored on a computer.

Deep muscle temperature is measured with a T thermocouple probe and wire, part No. IT-18 produced by Physitemp Instruments, Inc., Clifton, N.J. USA. The thermocouple is 24 gauge with a time constant of 0.3 seconds. The thermocouple is inserted into the tissue in a 22 gauge needle.

Prior to measuring deep muscle temperature, a subject is seated for 20 minutes in a 22° C. room. During the 20 minutes, the thermistor and thermocouple are placed on and under the skin, respectively. The area of the subject where the thermistor and thermocouple are located is scanned with a laser Doppler imager to measure skin blood flow. A heating device or modality to be tested (for example, conventional dry heat wrap, a system of the present invention, a whirlpool, a hydrocollator, etc.) is applied for a period of time that matches standard clinical therapy protocols for the heating modality used. After the test period the tested area of the subject is scanned again to measure skin blood flow. After the end of the test period, the thermistor and thermocouple are removed and the area where the thermocouple is placed is inspected and cleaned. Every 5 minutes during an experiment, the subject is asked to circle, on a 10-point visual analogue scale, the subject's perception of the heat and degree of satisfaction with the heating modality.

The thermocouple is placed into the quadriceps tissue 2.5 cm from the surface of the skin using a needle to penetrate the skin. To place the thermocouple into the tissue, a needle is inserted at a 60 degree angle to the skin, with depth verified by ultrasound imaging. Once the thermocouple is inserted, the needle is removed and the sterile thermocouple is left in place in the tissue. The limb of the subject does not move during the test period to minimize any potential trauma to the limb. To ensure sterility the thermocouple assembly is sterilized with CIDEX for one hour prior to use, and then washed in sterile saline.

The thermocouple is placed into the deep muscle tissue, and not the fat layer. Placement is confirmed by ultrasonic measurement (Sonosite 180, Seattle Wash. USA) of the subject's upper thigh.

The output of the thermocouple is transduced by an Iso-thermex digital thermometer system certified for human and hospital use. Such a device is accurate to 0.1% and is produced by Columbus Instruments, Columbus, Ohio, USA.

The thermocouple is left in place throughout testing and for 15 minutes after removal of the heating modality. A system of the present invention is left in place for 1 hour.

Skin blood flow can be measured using an infrared laser Doppler flow meter, (TST 140 probe from Biopac systems, Goleta, Calif., USA). The device has a 3 g flat probe with an active surface area of 1 square cm. The probe is plugged into a LDF 100C amplifier and digitized to 2,000 samples per second with a 16 bit analog to digital converter (Biopac Systems, NP150, Goleta, Calif., USA). The unit is warmed for 30 minutes prior to flow measurements. The flow probe is calibrated prior to and at the end of an experiment. The tissue volume sampled by the probe is 1 $mm^3$. A test subject sits in a 22° C. room for 20 minutes prior to an experiment, during which time blood flow is measured.

Measurements are taken prior to applying a heating modality, immediately after removing a heating modality, and at 5, 10 and 15 minutes after removing a heating modality.

Skin and muscle temperature over time, and skin blood flow can then be analyzed.

Cardiac work is a calculated representation of the cardiac effort being expended by the body under certain conditions. Cardiac Work is defined as a product of the heart rate and a mathematical average of the diastolic and systolic blood pressure.

Starting Cardiac work=the average starting heart rate×starting average blood pressure.

Starting average blood pressure=((average starting systolic blood pressure−average starting diastolic blood pressure)×0.33+average starting diastolic blood pressure)/100.

Finishing Cardiac work=the average finishing heart rate×finishing average blood pressure.

Finishing average Blood pressure=((average finishing systolic blood pressure−average finishing diastolic blood pressure)*0.33+average finishing diastolic blood pressure)/100.

Difference in cardiac workload=Starting Cardiac workload−Finishing Cardiac workload.

Heart rate is measured in beats per minute. Heart rate is measured by an individual feeling a test subject's radial pulse over a period of one minute.

Blood pressure is measured by auscultation of the right arm of a test subject with an air sphygmomanometer. Systolic and diastolic pressures are determined according to the procedure and standards of the American Heart Association and provided in mmHg, with systolic being the first tapping and diastolic being a change from a tap to a muffle. The blood pressure cuff is inflated to 200 mmHg and the pressure reduced at 3 mmHg intervals per second.

The system can also provide perception of comfort and pain relief within about 10 minutes of initiation of heating of the system. To determine comfort level and pain relief, a 0-10 point visual analog scale is used to measure subjective comfort. Such a scale can be used, for example, during deep muscle testing described above in a test subject's leg. Comfort and pain relief is measured before a heating modality is applied, and every 5 minutes during a first hour, then can be measured each hour thereafter for longer experiments. After a heating modality is removed, comfort and pain relief is measured at 5, 10, and 15 minutes. Alternatively pain relief may be assessed by evaluating range of motion before and after treatment with the moist heat system.

The system of the present invention also generates from about 0.05 mg water vapor/min/$cm^2$ to about 2.5 mg water vapor/min/$cm^2$ of water vapor generating portion, and alternatively from about 0.1 mg water vapor/min/$cm^2$ to about 2.0 mg water vapor/min/$cm^2$ of water vapor generating portion, wherein the water vapor delivers moisture to the surface of the skin via condensation onto the surface of the skin.

The amount of water vapor generated, and water vapor generation rate can be measured by measuring the weight change of a system of the present invention, or other exothermic heating device, from before initiation of heating to after the system is spent, and over time during use of the system. To measure and record the weight change, a Mettler-Toledo Balance Model PG503-S is connected to a computer running Toledo BalanceLink (Mettler Toledo AG, CH-8606 Greaifensee, phone +41 44 944 22 11) software using a RS232C interface cable. Prior to testing the balance is calibrated according to the manufacturer's instructions. A 4 inch thick stero-foam sheet is placed on top of the scale of the balance and the balance is zeroed.

The system to be tested is removed from an air-tight foil pouch where it is stored after manufacture, is placed in the center of the stero foam sheet with the latent heat delivery surface facing up so that water vapor may escape, and data recording initiated.

The starting weight of the exothermic heating device and the weight of the exothermic heating device thereafter are recorded until the system is spent, and thereby moisture loss from the start to the end of the reaction can be measured.

The amount of weight loss is correlated to the amount of water loss, which estimates the amount of water vapor generated during the reaction. With an exothermic composition such as that of the present invention, because none of the other components of the exothermic composition is lost during the reaction, and water is not consumed as part of the reaction, weight lost can be correlated to water lost and water vapor generated. Measurements based on weight lost, and calculations of water vapor generated are approximations because during the course of the reaction iron oxide is produced, and thus some weight is also gained during the course of the reaction. However, a minimal amount of iron oxide is produced and thus a de minimus amount of weight is gained. Thus, the amount of weight lost approximates the amount of water lost.

Amount of water vapor generated per area of skin of a user can be calculated by dividing the total amount of water vapor generated by the system by the area of skin to which a system is applied. Water vapor generated per unit time can also be calculated by dividing the amount of water vapor generated by a system by the duration of water vapor generation. One of ordinary skill in the art would understand how to perform such calculations, either manually or using computer software.

In addition, the system can increase skin moisture level by at least about 300% versus skin moisture level prior to application of the system, over a time period of less than about 30 minutes.

Amount of skin moisture and increase in skin moisture is measured with a Corneometer 810 capacitance skin moisture meter (Courage Khazaka Electronics, Cologne, Del.). The corneometer determines the humidity level of the stratum corneum of the skin by electrical capacitance. Alteration in skin hydration level results in a change in capacitance. The capacitance probe is applied to the skin for one second at a pressure of 7.1N/$cm^2$. The degree of skin capacitance is indicated from 1-100 units. One unit represents a water content of the stratum corneum of 0.02 mg/$cm^2$ at a measuring depth of 20 nm. Very dry skin is less than 30 units, dry skin is 30-45 units and sufficiently moisturized skin is greater than 45 units.

Tissue (i.e. skin in this case) capacitance is measured by applying electromagnetic waves at a frequency of 100,000 cycles/second (Hz), to a depth of 20 nm, to image the skin surface. The probe is placed on the skin of a test subject at a location desired to be studied. Prior to testing, the subject sits in a room at about 22° C. and 40% relative humidity for 20 minutes, to allow the skin to come to a normalized condition. Capacitance, from which skin moisture is calculated, is measured before and immediately after removal of the heating modality.

Methods of Use

A thermal device may be solely a moist heat system or a moist heat system used in conjunction with conventional conduction heating system. For example, a thermal device may comprise at least one moist heat cell and at least one dry heat cell may be incorporated in a thermal device. This configuration may be useful, for example, in providing heat and moist heat in a regulated manner to facilitate delivery of an aromatic substance or a therapeutic agent.

The present invention can provide methods of delivering consistent, safe, efficient, and sustained heat in a portable form to provide: pain relief, deep muscle heating, increased blood flow, reduced cardiac work, relaxation, wound healing, delivery of moisture, delivery of actives, body warming, respiratory relief, skin hydration, enhanced sleep, physical therapy, and combinations thereof depending on the shape, size and form of the system—i.e. body wrap, facial wrap, bandage, blanket, and the like.

An embodiment of the present invention includes a method of providing deep tissue heating comprising:
  (a) providing a portable moist heat system comprising a water vapor generating portion comprising a water vapor source and a heat source; and a water vapor-air regulating portion, said water vapor-air regulating portion comprising a water vapor-air mixing layer, and a water vapor-air distribution layer; said water vapor generating portion and said water vapor-air regulating portion being in fluid communication; and said water vapor-air regulating portion having a latent heat delivery surface disposed adjacent the water vapor-air regulating portion;
  (b) applying the system to the skin of a user;
  (c) supplying a water vapor-air mixture generated by the system to the skin of the user; and
  (d) transferring heat to the skin of the user, wherein the system transfers heat to the skin of a user and wherein from about 15% to about 95% of heat to a user as latent heat of condensation while maintaining skin temperature less than about 43° C.

The method can provide from about 75 W/m$^2$ to about 500 W/m$^2$, alternatively from about 100 W/m$^2$ to about 200 W/m$^2$, alternatively from about 200 W/m$^2$ to about 500 W/m$^2$, and alternatively from about 300 W/m$^2$ to about 500 W/m$^2$ of heat flux.

In addition, the method can comprise the step of providing a skin surface temperature of at least about 36° C. within about 5 minutes of initiation of heating of the system. The method also can provide a tissue temperature of at least about 38° C., at a depth of at least about 2.5 cm below an outer surface of the skin, within about 60 minutes from initiation of heating of the system, while maintaining a temperature of the outer surface of the skin of less than about 43° C.

An embodiment of the present invention also includes a method of providing rapid pain relief comprising:
  (a) providing a portable moist heat system comprising a water vapor generating portion comprising a water vapor source and a heat source; and a water vapor-air regulating portion, said water vapor-air regulating portion comprising a water vapor-air mixing layer, and a water vapor-air distribution layer; said water vapor generating portion and said water vapor-air regulating portion being in fluid communication; and said water vapor-air regulating portion having a latent heat delivery surface disposed adjacent said water vapor-air regulating portion;
  (b) applying the system to the skin of a user;
  (c) initiating heating of the system; and
  (d) supplying a water vapor-air mixture generated by the system to the skin of the user; wherein the system provides pain relief within about 60 minutes from initiation of heating of the system while maintaining skin temperature less than about 43° C.

The method can further comprise the steps of providing a pain-relieving active; and delivering the active through the skin. A pain relieving active can be incorporated into the water vapor generating portion, into the water vapor source, or into the water vapor-air regulating portion. A pain relieving active can also be incorporated into a separate device that is used in conjunction with the system of the present invention to deliver the pain relieving active through the skin.

An embodiment of the present invention also includes a method of increasing blood flow comprising:
  (a) providing a portable moist heat system comprising a water vapor generating portion comprising a water vapor source and a heat source; and a water vapor-air regulating portion, said water vapor-air regulating portion comprising a water vapor-air mixing layer, and a water vapor-air distribution layer; said water vapor generating portion and said water vapor-air regulating portion being in fluid communication; and said water vapor-air regulating portion having a latent heat delivery surface disposed adjacent said water vapor-air regulating portion;
  (b) applying the system to the skin of a user;
  (c) initiating heating of the system; and
  (d) increasing blood flow, in an area of the skin of the user where the system is applied, of from about 2 to about 9 times versus blood flow of the area of skin prior to application of the system, during a time period the system is applied to the skin of a user; while maintaining skin temperature less than about 43° C.

The present invention also includes a method of providing reduced cardiac work, and relaxation, comprising:
  (a) providing a portable moist heat system comprising a water vapor generating portion comprising a water vapor source and a heat source; and a water vapor-air regulating portion, said water vapor-air regulating portion comprising a water vapor-air mixing layer, and a water vapor-air distribution layer; said water vapor generating portion and said water vapor-air regulating portion being in fluid communication; and said water vapor-air regulating portion having a latent heat delivery surface disposed adjacent said water vapor-air regulating portion;
  (b) applying the system to the skin of a user;
  (c) initiating heating of the system; and
  (d) reducing cardiac work by at least about 4% during a time period the system is applied to the skin of a user while maintaining skin temperature less than about 43° C. The time period the system is applied to the skin of a user can be at least about 1 hour.

An embodiment of the present invention also comprises a method of providing moisture to the skin comprising:
  (a) providing a portable moist heat system comprising a water vapor generating portion comprising a water vapor source and a heat source; and a water vapor-air regulating portion, said water vapor-air regulating portion comprising a water vapor-air mixing layer, and a water vapor-air distribution layer; said water vapor generating portion and said water vapor-air regulating portion being in fluid communication; and said water vapor-air regulating portion having a latent heat delivery surface disposed adjacent said water vapor-air regulating portion;
  (b) applying the system to the skin of a user; initiating heating of the system;
  (c) generating from about 0.05 mg water vapor/min/cm$^2$ of water vapor generating portion to about 10 mg water vapor/min/cm$^2$ of water vapor generating portion, wherein the water vapor delivers moisture to the surface of the skin via condensation onto the surface of the skin.

The method can further comprise the step of increasing skin moisture level by at least about 300% versus skin moisture level prior to application of the system, over a time period of less than about 60 minutes. The method can also comprise the steps of providing a cosmetic active; and delivering the cosmetic active to the skin.

An embodiment of the present invention also includes a method of providing a benefit to a user comprising:
  (a) providing a portable moist heat system comprising a water vapor generating portion comprising a water vapor source and a heat source; and a water vapor-air regulating portion, said water vapor-air regulating portion comprising a water vapor-air mixing layer, and a water vapor-air distribution layer; said water vapor generating portion and said water vapor-air regulating portion being in fluid communication; and said water vapor-air regulating portion having a latent heat delivery surface disposed adjacent said water vapor-air regulating portion;
  (b) applying said system to a surface of a user wherein the latent heat delivery surface is located proximate the surface of the user.
  (c) initiating heating of said system; and
  (d) transferring moist heat to the skin of the user at a preselected temperature range, wherein the moist heat is about 15% to about 95% latent heat of condensation.

The method can further comprise further comprising the step of providing a benefit selected from the group consisting of reducing cardiac work by at least about 4% during a time period said system is applied to the skin of a user; increasing blood flow, in an area of the skin of said user where said system is applied, of from about 3 to about 9 times versus blood flow of said area of skin prior to application of said system; providing relaxation; providing wound healing; providing respiratory relief; providing body warming; providing skin hydration providing enhanced sleep; providing physical therapy, promoting or enhancing post-operative recovery, promoting or enhancing injury recovery and combinations thereof.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified concentrations are weight-weight percents, unless otherwise specified.

Examples 1-3

Water Vapor Source

The water vapor source exemplified below is exothermic heat cells filled with a particulate exothermic composition for use in the water vapor generating portion of the system of the present invention.

The particulate exothermic compositions exemplified below are prepared by using conventional blending techniques to form the particulate exothermic compositions, wherein the resultant compositions provide for the construction of heat cells of the present invention.

A pre-mix is prepared by adding activated carbon and water into a blender or mixer such as a Littleford Day Mixer, and mixing for about ten minutes. A polyacrylate absorbent gelling material is then added, and the mixture is mixed for about 10 minutes. Next, sponge iron powder is added to the mixer, and the resultant pre-mix is mixed for about 5 minutes.

Approximately 2.2 g of the resultant pre-mix composition are added to each preformed pocket, which pockets have been created with a vacuum to form the pockets, in a sheet of polypropylene/EVA coextruded film (e.g. 60% PP/40% EVA coextruded RMS #GCAS10045989 24.7 gsm 1.4 mil (Clopay, Augusta, Ky.) film).

Next, a brine solution is prepared by adding water, sodium chloride, and optionally sodium thiosulfate into a mixer and mixing for about fifteen minutes. The resultant brine solution is then rapidly dosed onto the pre-mix composition.

An aerated surface of 100% polypropylene, finished part #CTM4417064, 44.1 gsm SMMS (First Quality Nonwovens, McElhattan, Pa.) non-woven material is placed over the pockets containing the pre-mix and brine, facing the EVA side of the preformed pocket-containing. The film sheet and SMMS are bonded together using a low heat, forming a unified structure. The resulting unified structure contains heat cells containing the particulate exothermic composition sealed in the pockets between the opposing surfaces of the aerated surface and the opposed film layer surface.

The heat cells begin to generate heat shortly after the brine is added to the particulate composition, therefore the top and bottom surfaces are bonded and the finished heat cells are quickly packaged in an air tight secondary packaging for future use.

Table 1 illustrates different particulate exothermic compositions of heat cells of the present invention.

TABLE 1

Particulate Exothermic Compositions

| Component | Composition 1 (Wt. %) | Composition 2 (Wt. %) | Composition 3 (Wt. %) |
|---|---|---|---|
| Iron powder (F-417, Hoeganaes Corp., New Jersey) | 60.40 | 56.75 | 58.70 |
| Activated Carbon (NuChar-SN, MeadWestvaco, Covington, VA) | 4.05 | 3.81 | 3.94 |
| Absorbent Gelling Material (Sodium polyacrylate, Nippon Shokubai, Chattanooga, TN) | 5.09 | 4.78 | 4.94 |
| Sodium Chloride | 3.02 | 3.47 | 1.38 |
| Sodium Thiosulfate | 0.38 | 0.43 | — |
| Water | 27.06 | 30.76 | 31.04 |

Example embodiments of the present invention are described below with reference to the FIG. 3 and FIG. 1. The same symbols represent the same structural elements throughout.

Figure 3:
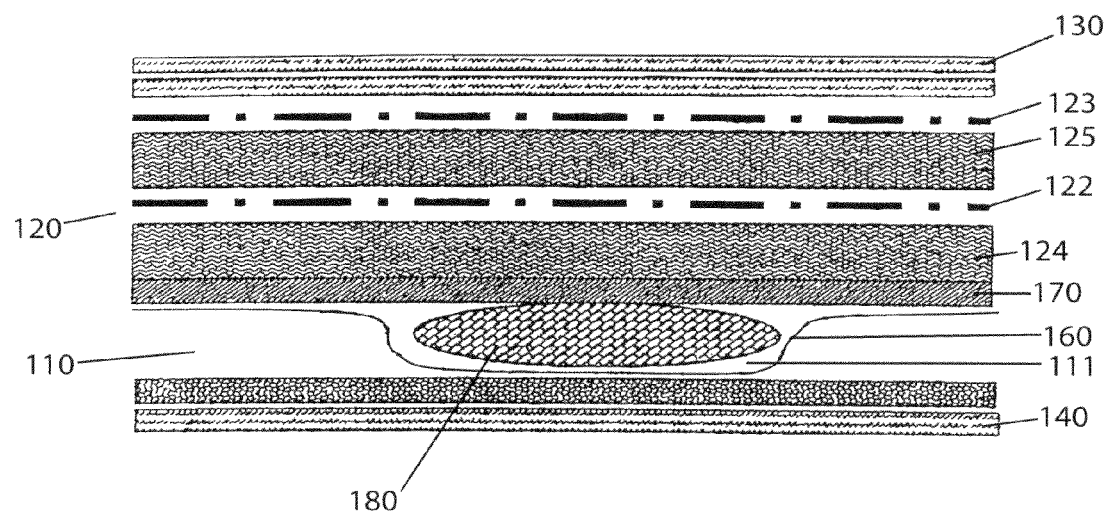
FIG. 3 is a cross sectional schematic diagram of an embodiment of the present invention.

FIG. 3 illustrates an embodiment of a moist heat delivery system having two water vapor-air mixing layers and two water vapor-air distribution layers as part of a water vapor-air regulating portion. Referring to FIG. 3, the water generating portion 110 comprises heat cell 180. Heat cell 180 is constructed according to Example 1 using the Composition of Table 1 above. Adjacent the water generating portion 110 is a water vapor-air regulating portion 120. Adjacent a second side of the water generating portion 110 is the external surface 140 comprising an insulative layer and an outermost layer.

The heat cell 180 has a particulate exothermic composition dosed in a pocket 111 formed in an opposed surface 160 of non-air permeable, non-moisture permeable polypropylene/EVA film layer (e.g. 60% PP/40% EVA coextruded RMS #GCAS10045989 24.7 gsm 1.4 mil (Clopay, Augusta, Ky.)) opposing a polypropylene SMMS (e.g. 100% Polypropylene 34 gsm SB/4 gsm M/4 gsm M/34 gsm SB, Code W502FWH634, 76 gsm (Polymer Group Inc., Waynesboro, Va.)) aerated surface 170.

The external surface 140 is adjacent to opposed surface 160 and comprises two layers including a 1/16 inch insulative polypropylene foam layer 162 (e.g. 100% PP 1/16"MicroFoam RMS #95818584 16 gsm (Pregis, Wurtland, Ky.) and an outermost polypropylene non-woven layer 164.

Adjacent the aerated surface 170 is a 3 mm thick first water vapor-air mixing layer 124 of high loft polyethylene/polyester non-woven batting (e.g. 70% 9 dpfPET/PE BICO/30% 12 dpf hollow PET fibers RMS #95169555 84 gsm through air bonded (Libeltex, Meulebeke, Belgium). Adjacent the first water vapor-air mixing layer 124 is a first water vapor-air distribution layer 122 of 1/16 inch thick perforated polypropylene foam (e.g. 100% PP 1/16" MicroFoam RMS #95818584 16 gsm (Pregis, Wurtland, Ky.); altered internally via cutting dies to add perforation). Adjacent the first water vapor-air distribution layer 122 is a second 3 mm thick water vapor-air mixing layer 125 of high loft polyethylene/polyester non-woven batting of the same material as used in the first water vapor air mixing layer 124. Adjacent the second water vapor-air mixing layer 125 is a second water vapor-air distribution layer 123 of 1/16 inch thick perforated polypropylene foam of the same material as used in the first water vapor-air distribution layer 122. Attached to the second water vapor-air distribution layer 123 is the latent heat delivery surface 130 comprising two skin-contact layers of polypropylene non-woven material (e.g. 50/50 Polypropylene/Polyethylene BICO Part #236YLJO09P 80 gsm (Fiberweb, Washougal, Wash.), internally altered through mechanical deformation). The layers are sealed together around the periphery of the layers to form a system.

Referring for FIG. 1, FIG. 1 illustrates an embodiment of a moist heat system having only one water vapor-air mixing layer and one water vapor-air distribution layer. Referring to FIG. 1, the heat cell 80 is constructed according to Example 1 above using the composition of Table 1. The heat cell 80 has a particulate exothermic water vapor generating composition dosed in a pocket 11 formed in an opposed surface of polypropylene/EVA (e.g. 60% PP/40% EVA coextruded RMS #GCAS10045989 24.7 gsm 1.4 mil (Clopay, Augusta, Ky.)) film layer 60 opposing a 100% polypropylene (i.e. finished part #CTM4417064, 44.1 gsm SMMS (First Quality Nonwovens, McElhattan, Pa.) SMMS aerated surface 70.

The external surface 40 is adjacent the opposed surface film layer 60 and comprises two layers including a 1/16 inch insulative polypropylene foam (e.g. MicroFoam RMS #95818584 16 gsm (Pregis, Wurtland, Ky.)) layer and an outer most polypropylene non-woven layer.

Adjacent the aerated surface 70 is the water vapor air mixing layer 24 which comprises a 3 mm thick water vapor-air mixing layer 20 of high loft polyethylene/polyester (e.g. 70% 9 dpfPET/PE BICO/30% 12 dpf hollow PET fibers RMS #95169555 84 gsm through air bonded (Libeltex, Meulebeke, Belgium)) non-woven batting. Adjacent the water vapor-air mixing layer 24 is a water vapor-air distribution layer 22 of 1/16 inch thick perforated polypropylene foam (e.g. 100% PP 1/16" MicroFoam RMS #95818584 16 gsm (Pregis, Wurtland, Ky.); altered internally via cutting dies to add perforation). Adjacent to the water vapor-air distribution layer 22 is the latent heat delivery surface 30 comprising two skin-contact layers of polypropylene non-woven material (e.g. 50/50 Polypropylene/Polyethylene BICO Part #236YLJ009P 80 gsm (Fiberweb, Washougal, Wash.), internally altered through mechanical deformation). The layers are sealed together around the periphery of the layers to form a system.

Figure 4:
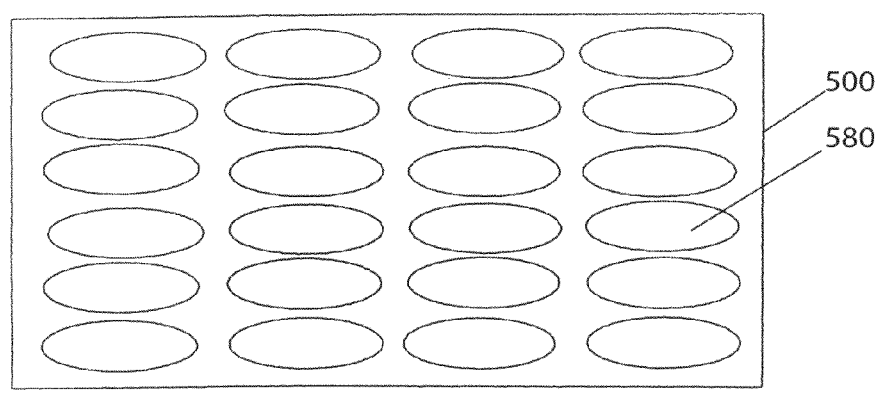
FIG. 4 is a top view of an embodiment of the present invention.

Referring to FIG. 4, FIG. 4 is a top plan view of an embodiment of a therapeutic device of the present invention 500 having a plurality of heat cells (e.g. twenty-four (24) heat cells) 580 forming a water vapor generating portion that comprises a particulate exothermic composition that includes a water vapor source and a heat source.

IR Imaging Examples

Figure 5A:
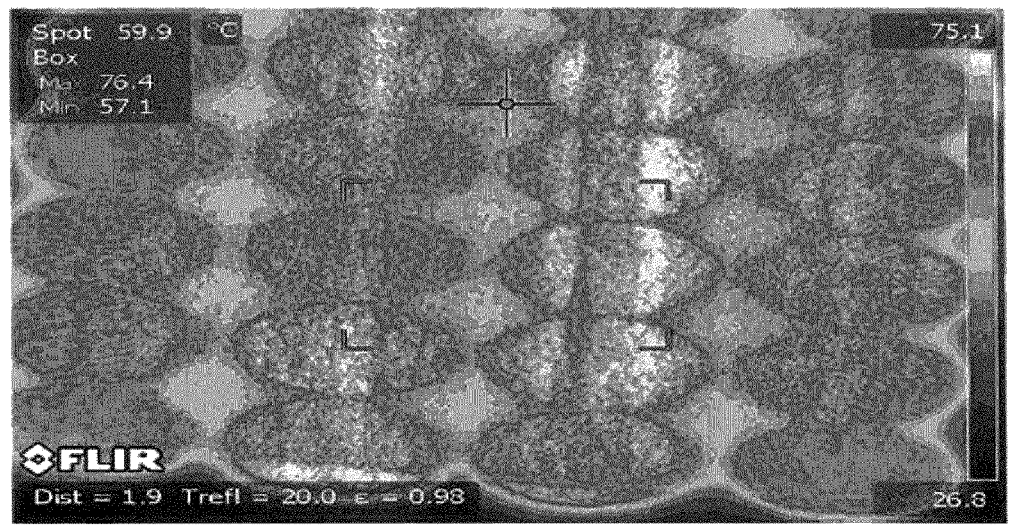
FIGS. 5a and 5b are infrared photographs of an embodiment of an activated portable moist heat delivery system.
Figure 5B:
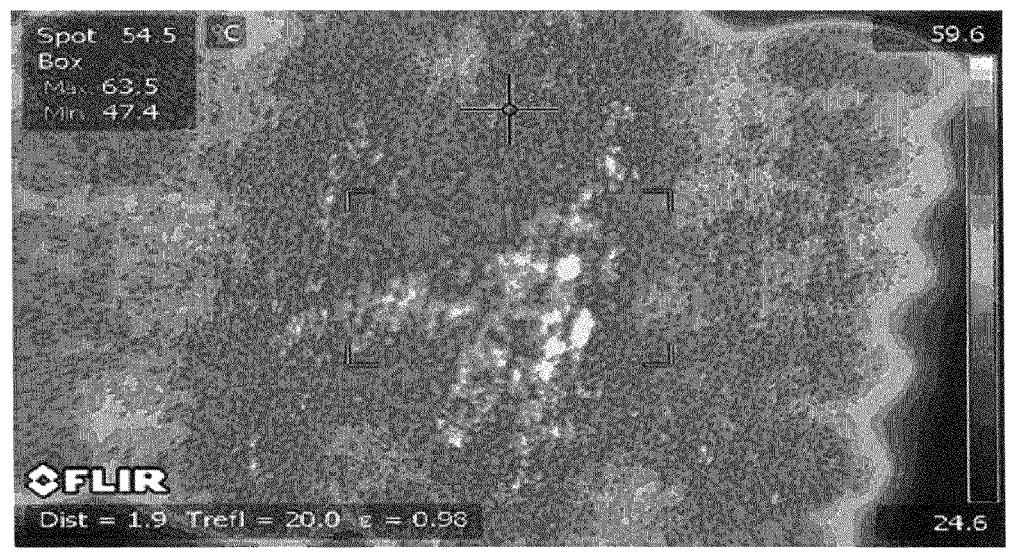

FIGS. 5A and 5B show IR images of an exemplary embodiment of the activated moist heat delivery system therapeutic device of the invention. FIG. 5A is a view of the external surface of an activated moist heat delivery system therapeutic device of the invention. As FIG. 5A shows the outlines of individual heat cells are visible on the exterior surface in the IR image. FIG. 5B is a view of the latent heat delivery surface of an activated moist heat delivery system therapeutic device of the invention. As FIG. 5B shows, the water vapor-air regulating portion facilitates dispersion and uniformity of heat over the latent heat delivery surface of the activated system. As FIG. 5B shows, the perimeter shapes of the individual heat cells are indiscernible in an IR image of the latent heat delivery surface of an activated system that is delivering heat to the latent heat delivery surface due to dispersion of the heat.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of providing a benefit to a user comprising:
    (a) providing a portable moist heat delivery system comprising a water vapor generating portion comprising a water vapor source and a heat source; and a water vapor-air regulating portion, said water vapor-air regulating portion comprising a water vapor-air mixing layer, and a water vapor-air distribution layer, said water vapor generating portion and said water vapor-air regulating portion being in fluid communication; and said water vapor-air regulating portion having a latent heat delivery surface disposed adjacent said water vapor-air regulating portion which delivers moist heat at a preselected temperature range;
    (b) applying said system to a skin surface of a user wherein the latent heat delivery surface is located proximate to said skin surface of said user;
    (c) initiating heating of said system; and
    (d) transferring moist heat to said skin of said user at a preselected temperature range, wherein the moist heat is about 15% to about 95% latent heat of condensation.

2. The method of claim 1 wherein said portable moist heat system is applied to a skin surface of a human user and wherein said human skin maintains a temperature of less than about 43° C. during the transfer of moist heat.

3. The method of claim 1 further comprising the step of providing a skin surface temperature of at least about 36° C. within about 5minutes of initiation of heating of said system.

4. The method of claim 1 further comprising the step of delivering moist heat to a tissue and providing a temperature of at least about 38° C., at a depth of at least about 2.5 cm below an outer surface of said skin, within about 60 minutes from initiation of heating of said system, while maintaining a temperature of said outer surface of said skin of less than about 43° C.

5. The method of claim 1 whereby the moist heat provides pain relief within about 60 minutes from said initiation of heating of said system, while maintaining user skin surface temperature less than about 43° C.

6. The method of claim 1 further comprising the steps of providing a pain-relieving active; and delivering said active through said skin.

7. The method of claim 1 providing further comprising the step of generating from about 0.05 mg water vapor/min/cm2 of water vapor generating portion to about 10 mg water vapor/min/cm2 of water vapor generating portion; wherein said water vapor delivers moisture to the surface of said skin via condensation onto said surface of the skin, while maintaining skin temperature less than about 43° C.

8. The method of claim 1 further comprising the step of providing a benefit selected from the group consisting of reducing cardiac work by at least about 4% during a time period said system is applied to said skin of said user; increasing blood flow, in an area of said skin of said user where said system is applied; of from about 3 to about 9 times versus blood flow of said area of skin prior to application of said system; providing relaxation; providing wound healing; providing respiratory relief; providing body warming; providing skin hydration; providing enhanced sleep; providing physical therapy, promoting post-operative recovery, promoting injury recovery, enhancing post-operative recovery, enhancing injury recovery, and combinations thereof.

* * * * *